US006649380B1

(12) United States Patent
Yano et al.

(10) Patent No.: US 6,649,380 B1
(45) Date of Patent: Nov. 18, 2003

(54) METHOD FOR CONTROLLING MOLECULAR WEIGHT OF POLYHYDROXYALKANOTE CONSTITUTED ON UNITS CONTAINING RESIDUE OF PHEYNYL-, THIENYL-, OR CYCLOHEXYL-STRUCTURE IN SIDE CHAIN OF MOLECULE

(75) Inventors: Tetsuya Yano, Kanagawa (JP); Takashi Kenmoku, Kanagawa (JP); Tsutomu Honma, Kanagawa (JP); Etsuko Sugawa, Kanagawa (JP); Tatsuki Fukui, Kanagawa (JP); Takeshi Imamura, Kanagawa (JP)

(73) Assignee: Canon Kabushiki Kaisha, Tokyo (JP)

( * ) Notice: Subject to any disclaimer, the term of this patent is extended or adjusted under 35 U.S.C. 154(b) by 0 days.

(21) Appl. No.: 10/373,038

(22) Filed: Feb. 26, 2003

(30) Foreign Application Priority Data

Feb. 28, 2002 (JP) ........................ 2002-054907
Feb. 14, 2003 (JP) ........................ 2003-036819

(51) Int. Cl.$^7$ ............................ C12P 7/62; C08G 63/06
(52) U.S. Cl. ...................... 435/135; 528/361; 528/364; 528/293; 524/765; 435/136; 435/142; 435/146; 435/874
(58) Field of Search ................. 528/361, 364; 524/765; 435/135, 136, 142, 146, 874

(56) References Cited

U.S. PATENT DOCUMENTS

| 5,191,016 | A | 3/1993 | Yalpani | 525/54.2 |
|---|---|---|---|---|
| 5,811,272 | A | 9/1998 | Snell et al. | 435/135 |
| 6,156,852 | A | 12/2000 | Asrar et al. | 525/450 |
| 6,521,429 | B2 | 2/2003 | Honma et al. | 435/135 |
| 2002/0052444 | A1 | 5/2002 | Imamura et al. | 525/107 |
| 2002/0160467 | A1 | 10/2002 | Honma et al. | 435/135 |

FOREIGN PATENT DOCUMENTS

| EP | 1 113 033 A2 | 7/2001 |
|---|---|---|
| EP | 1 130 042 A2 | 9/2001 |

(List continued on next page.)

OTHER PUBLICATIONS

Fengying Shi et al., "Use of Poly(ethylene glycol)s to Regulate Poly(3–hydroxybutyrate) Molecular Weight During *Alcaligenes eutrophus* Cultivations," 29 *Macromol.* 7753–7758 (1996).
European Search Report in Application No. 03004348.3 (May 15, 2003).
Katharina Fritzsche et al., "An Unusual Bacterial Polyester with a Phenyl Pendant Group," 191 *Makromol. Chem.* 1957–1965 (1990).

Y.B. Kim et al., "Preparation and Characterization of Poly($\beta$–hydroxyalkanoates) Obtained from *Pseudomonas oleovorans* Grown with Mixtures of 5–Phenylvaleric Acid and n–Alkanoic Acids," 24 *Macromol.* 5256–5260 (1991).
Joanne M. Curley et al., "Production of Poly(3–hydroxyalkanoates) Containing Aromatic Substituents by *Pseudomaonas oleovorans*," 29 *Macromol.* 1762–1766 (1996).
Suzette M. Aróstegui et al., "Bacterial Polyesters Produced by *Pseudomonas oleovorans* Containing Nitrophenyl Groups," 32 *Macromol.* 2889–2895 (1999).
Helmut Ritter et al., "Bacterial Production of Polyesters Bearing Phenoxy Groups in the Side Chain, 1 Poly(3–hydroxy–5–phenoxypentanoate–co–3–hydroxy–9 –phenoxy–nonanoate) from *Pseudomonas oleovorans*," 195 *Macromol. Chem. Phys.* 1665–1672 (1994).
Ohyoung Kim et al., "Bioengineering of Poly($\beta$–hydroxyalkanoates) for Advanced Material Applications: Incorporated of Cyano and Nitrophenoxy Side Chain Substituents," 41 (Supp. 1) *Can. J. Microbiol.* 32–43 (1995).
Richard A. Gross et al., "Cyanophenoxy–Containing Microbal Polyesters: Structural Analysis, Thermal Properties, Second Harmonic Generation and In–Vivo Biodegradability," 39 *Polymer International* 205–213 (1996).
Yasuo Takagi et al., "Biosynthesis of Polyhydroxyalkanoate with a Thiophenoxy Side Groups Obtained from *Pseudomonas putida*," 32 *Macromol.* 8315–8318 (1999).
A. Steinbüchel et al., "Molecular Basis for Biosynthesis and Accumulation of Polyhydroxyalkanoic Acids in Bacteria," 103 *FEMS Microbiol. Rev.* 217–230 (1992).
Leigh A. Madden et al., "Chain Termination in Polyhydroxyalkanoate Synthesis: Involvement of Exogenous Hydroxy–Compounds as Chain Transfer Agents," 25 *Intl. J. Biol. Macromol.* 43–53 (1999).
Gerhart Braunegg et al., "Polyhydroxyalkanoates, Biopolyesters from Renewable Resources: Physiological and Engineering Aspects," 65 *J. Biotechnol.* 127–161 (1998).
Richard Ashbey et al., "A Turable Switch to Regulate the Synthesis of Low and High Molecular Weight Microbal Polyesters," 62(1) *Biotechnol. Bioeng.* 106–113 (Jan. 1999).

*Primary Examiner*—Samuel A. Acquah
(74) *Attorney, Agent, or Firm*—Fitzpatrick, Cella, Harper & Scinto

(57) ABSTRACT

A method is provided for controlling the molecular weight of a polyhydroxyalkanoate containing at least one of a unit: —[OCH(($CH_2$)$_m$$R_1$)$CH_2$C(O)]— (m=1–8; $R_1$ is a residue having a ring structure of any of phenyl and thienyl structure), and a unit: —[OCH(($CH_2$)$_k$$C_6H_{11}$)$R_2$)$CH_2$C (O)]— (k=0–8; $R_2$ denotes a substituent on the cyclohexyl group including H, CN, $NO_2$, halogen atom, $CH_3$, $C_2H_5$, $C_3H_7$, $CF_3$, $C_2F_5$ or $C_3F_7$), wherein a microorganism is cultivated in the presence of a hydroxyl group-containing compound, which is capable of producing the polyhydroxyalkanoate from $R_3$($CH_2$)$_q$$CH_2$$CH_2$COOH (q=1–8; $R_3$ contains a residue having a ring structure of phenyl or thienyl) or $R_4$$C_6H_{10}$($CH_2$)$_r$$CH_2$$CH_2$COOH (r=0–8; $R_4$ denotes a substituent on the cyclohexyl group including H, CN, $NO_2$, halogen, $CH_3$, $C_2H_5$, $C_3H_7$, $CF_3$, $C_2F_5$, or $C_3F_7$).

12 Claims, No Drawings

FOREIGN PATENT DOCUMENTS

| | | |
|---|---|---|
| EP | 1 130 043 A2 | 9/2001 |
| EP | 1 188 782 A2 | 3/2002 |
| EP | 0 236 752 A2 | 9/2002 |
| EP | 1 236 754 A2 | 9/2002 |
| EP | 1 236 755 A2 | 9/2002 |
| EP | 1 245 605 A2 | 10/2002 |
| EP | 1 253 161 A2 | 10/2002 |
| EP | 1 253 162 A2 | 10/2002 |
| EP | 1 262 508 A2 | 12/2002 |
| EP | 1 275 727 A2 | 1/2003 |
| JP | 2000-72865 | 3/2000 |
| WO | WO 97/07153 | 2/1997 |

METHOD FOR CONTROLLING MOLECULAR WEIGHT OF POLYHYDROXYALKANOTE CONSTITUTED ON UNITS CONTAINING RESIDUE OF PHEYNYL-, THIENYL-, OR CYCLOHEXYL-STRUCTURE IN SIDE CHAIN OF MOLECULE

BACKGROUND OF THE INVENTION

1. Field of the Invention

The present invention relates to a method for controlling the molecular weight of a polyhydroxyalkanoate (PHA), a kind of polyester. More specifically, the present invention relates to a method for controlling the molecular weight of the PHA employing a microorganism which is capable of producing and accumulating the PHA in the cell.

2. Related Background Art

Many microorganisms have been reported to produce and accumulate poly-3-hydroxybutyric acid (PHB) or other PHA in the cells ("Seibunkaisei Purasutikku Handobukku (Biodegradable Plastics Handbook)", Biodegradable plastics Research Group, NTS K. K., pp.178–197 (1995)). These polymers are useful as various articles molded by melt processing or other processing similarly as conventional polymers. Moreover, these polymers, which are biodegradable, are completely degraded by a microorganism in the nature, not causing pollution in natural environment advantageously, differently from conventional synthetic high polymers. Furthermore, these diodegradable polymers are highly adaptable to a living body and are promising also for a medical soft material and other uses.

Such PHAs produced by a microorganism are known to have various compositions and structures depending on the kind of microorganism, culture medium composition, cultivation conditions, and other factors in the production. The control of the composition and structure of PHA has been studied for improvement of the physical properties of PHA.

The PHAs produced by microorganisms are roughly classified into two groups according to the biosynthesis mechanism. One group of PHAs are short-chain-length PHAs (hereinafter referred to as "scl-PHA(s)") typified by polyhydroxybutyric acid (PHB), polyhydroxyvaleric acid (PHV), and copolymers thereof: the other group of PHAs are medium-chain-length PHAs (hereinafter referred to as "mcl-PHA(s)") having medium-chain-length 3-hydroxyalkanoic acid of about 6–14 carbons as the units.

The former, scl-PHA, is formed from sugars such as glucose and gluconic acid, or acetyl-CoA which is an in-vivo metabolism product of organic acids such as lactic acid, pyruvic acid, and malic acid as the starting material by enzymatic dimerization and reduction into a polymer.

The latter, mcl-PHA, is formed enzymatically from an alkanoic acid as the starting material by CoA addition, dehydrogenation, and water addition through the β-oxidation pathway, a fatty acid degradation system, into a polymer.

As mentioned above, the respective groups of PHAs are synthesized through different biosynthesis pathways by action of different enzymes in vivo according to the results of detailed investigation.

Of the microorganisms producing the latter, mcl-PHAs, some microorganisms are known to produce PHAs having various functional groups and residues.

Among them, production of the PHAs having an aromatic ring in the unit is actively investigated in recent years.

Makromol.Chem., 191, 1957–1965 (1990) and Macromolecules, 24, 5256–5260 (1991) describe that *Pseudomonas oleovorans* produces a PHA containing 3-hydroxy-5-phenylvaleric acid as the unit from 5-phenylvaleric acid as the substrate.

Macromolecules, 29, 1762–1766 (1996) describes that *Pseudomonas oleovorans* produces a PHA containing 3-hydroxy-5-(4'-tolyl)valeric acid as the unit from 5-(4'-tolyl)valeric acid as the substrate.

Macromolecules, 32, 2889–2895 (1999) describes that *Pseudomonas oleovorans* produces a PHA containing 3-hydroxy-5-(2',4'-dinitrophenyl)valeric acid and 3-hydroxy-5-(4'-nitrophenyl)valeric acid as the units from 5-(2',4'-dinitrophenyl)valeric acid as the substrate.

Macromol.Chem.Phys., 195, 1665–1672 (1994) describes that *Pseudomonas oleovorans* produces a PHA copolymer of 3-hydroxy-5-phenoxyvaleric acid and 3-hydroxy-9-phenoxynonanoic acid from 11-phenoxyundecanoic acid as the substrate.

Japanese Patent Publication No. 2989175 discloses homopolymers having a 3-hydroxy-5-(monofluorophenoxy) pentanoate ($3H_5$(MHP)P) unit or a 3-hydroxy-5-(difluorophenoxy)pentanoate ($3H_5$(DHP)P) unit, and copolymers having at least the $3H_5$(MFP)P unit or $3H_5$(DFP)P unit synthesized by *Psudomonas putida* (Pseudomanas Genus); and a process for synthesis of the above polymers. Thereby, a polymer having a mono- or di-fluorine-substituted phenoxy group at side chain ends can be synthesized by assimilation of a substituted long-chain fatty acid, the polymer having stereoregularity and water repellency with retention of the high melting point and high processability.

Cyano- or nitro-substituted polymers are investigated besides the above fluorine-substituted polymers.

Can.J.Microbiol., 41, 32–43 (1995), and Polymer International, 39, 205–213 (1996) describe production of PHAs containing 3-hydroxy-p-cyanophenoxyhexanoic acid or 3-hydroxy-p-nitrophenoxyhexanoic acid as the monomer unit from octanoic acid and p-cyanophenoxyhexanoic acid or p-nitrophenoxyhexanoic acid as the substrate by employing *Pseudomonas oleovorans* ATCC29347 strain and *Pseudomonas putida* KT2442 strain.

Macromolecules, 32, 8315–8318 (1999) and Polymer Preprints, Japan, 49(5), 1034 (2000) describe capability of *Pseudomonas putida* 27N01 strain to produce PHA copolymers containing 3-hydroxy-5-thiophenoxyvaleric acid and 3-hydroxy-7-thiophenoxyheptanoic acid from 11-thiophenoxyvaleric acid as the substrate.

For practical application of the PHAs, control of the molecular weight is attempted to broaden the application field thereof.

U.S. Pat. No. 6,156,852 discloses the decrease of the number-average molecular weight in biosynthesis of PHB by employing *Ralstonia eutropha, Ralstonia latus*, and *Comamonas testosteroni* as the producing microorganism strain by addition of a diol such as ethylene glycol, neopentyl glycol, propylene glycol, butanediol, hexanediol, and octanediol; butanetriol, polypropylene glycol, glycerol, hydroquinone, benzene-dimethanol, pentaerithritol, and derivatives thereof; or a sugar alcohol such as sorbitol and mannitol to the culture medium. These items are described in detail as chemical reports in Biotechnology and Bioengineering, 62, 106–113 (1999), and International Journal of Biological Macromolecules, 25, 43–53 (1999).

These techniques have merits of controlling the molecular weight in the PHA biosynthesis process without using a chemical substance such as an acid or a base. The PHAs having a functional group such as the phenyl group described above are also required to be controlled in the molecular weight for broadening the practical application field. However, no technique therefore has been developed yet.

SUMMARY OF THE INVENTION

The present invention provide a method for controlling the molecular weight of a polyhydroxyalkanoate having units of a residue containing a phenyl-, thienyl-, or cyclohexyl-structure in the side chain of the molecule.

After comprehensive study to solve the above problems, the inventors of the present invention achieved the invention described below.

The present invention provides a method for controlling the molecular weight of a polyhydroxyalkanoate containing at least one of 3-hydroxy-ω-substituted alkanoic acid units represented by Chemical Formula (1):

$$\begin{array}{c}\text{(1)}\end{array}$$

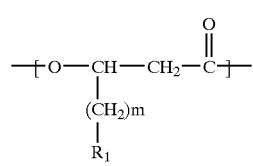

$m = 1-8$ (in the above formula, m is an integer selected from the numerical range shown with the Chemical Formula; $R_1$ is a residue having a ring structure of any one selected from the group consisting of a phenyl structure and a thienyl structure; and in the presence of plural units, m and $R_1$ are selected independently for the respective units), and 3-hydroxy-ω-cyclohexylalkanoic acid units represented by Chemical Formula (2):

$$\begin{array}{c}\text{(2)}\end{array}$$

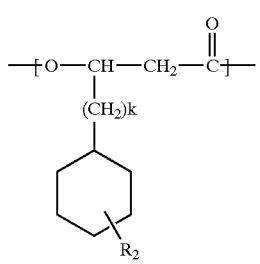

$k = 0-8$ (in the above formula, $R_2$ denotes a substituent on the cyclohexyl group selected from the group consisting of H atom, CN, $NO_2$, halogen atom, $CH_3$, $C_2H_5$, $C_3H_7$, $CF_3$, $C_2F_5$ and $C_3F_7$; k is an integer selected from the numerical range shown with the Chemical Formula; and in the presence of plural units, k and $R_2$ are selected independently for the respective units), wherein a microorganism is cultivated, in the presence of a hydroxyl group-containing compound, which is capable of producing the polyhydroxyalkanoate containing at least one of the units represented by Chemical Formula (1) or (2) from an ω-substituted alkanoic acid represented by Chemical Formula (3):

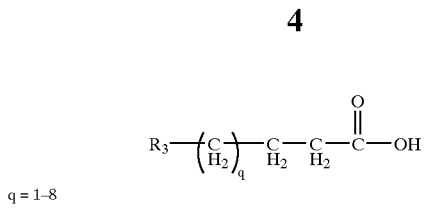

$q = 1-8$ (in the above formula, q is an integer selected from the numerical range shown with the Chemical Formula; $R_3$ is a residue having a ring structure of any one selected from the group consisting of a phenyl structure and a thienyl structure; and in the presence of plural units, q and $R_3$ are selected independently for the respective units), or ω-cyclohexylalkanoic acid represented by Chemical Formula (4):

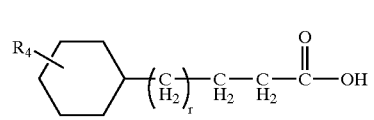

$r = 0-8$ (in the above formula, $R_4$ denotes a substituent on the cyclohexyl group selected from the group consisting of H atom, CN, $NO_2$, halogen atom, $CH_3$, $C_2H_5$, $C_3H_7$, $CF_3$, $C_2F_5$ and $C_3F_7$; and r is an integer selected from the numerical range shown with the Chemical Formula; and in the presence of plural units, $R_4$ and r are selected independently for the respective units).

Here, $R_1$, and $R_3$ in Chemical Formula (1) or (3), namely the residue having the phenyl structure or the thienyl structure includes specifically the groups represented by Chemical Formulas (5) to (15):

a substituted or unsubstituted phenyl group represented by General Formula (5):

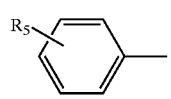

(in the above formula, $R_5$ denotes a substituent on the aromatic ring selected from the group consisting of H atom, halogen atom, CN, $NO_2$, $CH_3$, $C_2H_5$, $C_3H_7$, vinyl, $COOR_{51}$ (for $R_1$ only; $R_{51}$ is a substituent selected from the group consisting of H atom, Na atom and K atom), $CF_3$, $C_2F_5$ and $C_3F_7$; and in the presence of plural units, the above definition is applied independently of the respective units);

a substituted or unsubstituted phenoxy group represented by General Formula (6):

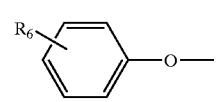

(in the above formula, $R_6$ denotes a substituent on the aromatic ring selected from the group consisting of H atom, halogen atom, CN, $NO_2$, $CH_3$, $C_2H_5$, $C_3H_7$, $SCH_3$, $CF_3$, $C_2F_5$ and $C_3F_7$; and in the presence of plural units, the above definition is applied independently of the respective units);

a substituted or unsubstituted benzoyl group represented by General Formula (7):

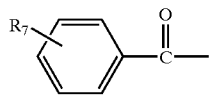
(7)

(in the above formula, $R_7$ denotes a substituent on the aromatic ring selected from the group consisting of H atom, halogen atom, CN, $NO_2$, $CH_3$, $C_2H_5$, $C_3H_7$, $CF_3$, $C_2F_5$ and $C_3F_7$; and in the presence of plural units, the above definition is applied independently of the respective units);

a substituted or unsubstituted phenylsulfanyl group represented by General Formula (8):

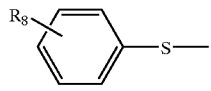
(8)

(in the above formula, $R_8$ denotes a substituent on the aromatic ring selected from the group consisting of H atom, halogen atom, CN, $NO_2$, $COOR_{81}$, $SO_2R_{82}$ ($R_{81}$ is a substituent selected from the group consisting of H, Na, K, $CH_3$ and $C_2H_5$; $R_{82}$ is a substituent selected from the group consisting of OH, ONa, OK, halogen atom, $OCH_3$ and $OC_2H_5$), $CH_3$, $C_2H_5$, $C_3H_7$, $(CH_3)_2$—CH and $(CH_3)_3$—C; and in the presence of plural units, the above definition is applied independently of the respective units);

a substituted or unsubstituted (phenylmethyl)sulfanyl group represented by General Formula (9):

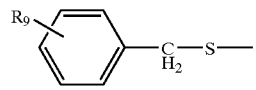
(9)

(in the above formula, $R_9$ denotes a substituent on the aromatic ring selected from the group consisting of H atom, halogen atom, CN, $NO_2$, $COOR_{91}$, $SO_2R_{92}$ ($R_{91}$ is a substituent selected from the group consisting of H, Na, K, $CH_3$ and $C_2H_5$; $R_{92}$ is a substituent selected from the group consisting of OH, ONa, OK, halogen atom, $OCH_3$ and $OC_2H_5$), $CH_3$, $C_2H_5$, $C_3H_7$, $(CH_3)_2$—CH and $(CH_3)_3$—C; and in the presence of plural units, the above definition is applied independently of the respective units);

a 2-thienyl group represented by Chemical Formula (10):

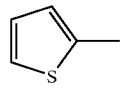
(10)

a 2-thienylsulfanyl group represented by Chemical Formula (11):

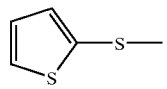
(11)

a 2-thienylcarbonyl group represented by Chemical Formula (12):

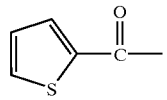
(12)

a substituted or unsubstituted phenylsulfinyl group represented by General Formula (13) (for $R_1$ only)

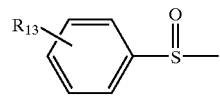
(13)

(in the above formula, $R_{13}$ denotes a substituent on the aromatic ring selected from the group consisting of H atom, halogen atom, CN, $NO_2$, $COOR_{131}$, $SO_2R_{132}$ ($R_{131}$ is a substituent selected from the group consisting of H, Na, K, $CH_3$ and $C_2H_5$; $R_{132}$ is a substituent selected from the group consisting of OH, ONa, OK, halogen atom, $OCH_3$ and $OC_2H_5$), $CH_3$, $C_2H_5$, $C_3H_7$, $(CH_3)_2$—CH and $(CH_3)_3$—C; and in the presence of plural units, the above definition is applied independently of the respective units);

a substituted or unsubstituted phenylsulfonyl group represented by General Formula (14) (for $R_1$ only)

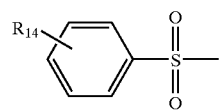
(14)

(in the above formula, $R_{14}$ denotes a substituent on the aromatic ring selected from the group consisting of H atom, halogen atom, CN, $NO_2$, $COOR_{141}$, $SO_2R_{142}$ ($R_{141}$ representing H, Na, K, $CH_3$ and $C_2H_5$; $R_{142}$ is a substituent selected from the group consisting of OH, ONa, OK, halogen atom, $OCH_3$ and $OC_2H_5$), $CH_3$, $C_2H_5$, $C_3H_7$, $(CH_3)_2$—CH and $(CH_3)_3$—C; and in the presence of plural units, the above definition is applied independently of the respective units); and a (phenylmethyl)oxy group represented by Chemical Formula (15):

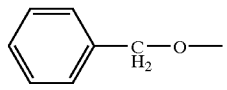
(15)

The hydroxyl group-containing compound is at least the one selected from the group consisting of alcohols, diols, triols, alkylene glycols, polyethylene glycols, polyethylene oxides, alkylene glycol monoesters, polyethylene glycol monoesters, and polyethylene oxide monoesters.

More specifically, the alcohols, diols, and triols may include linear and branched alcohols, diols, and triols of 3–14 carbons.

The alkylene glycols and alkylene glycol monoesters may be compounds of 2–10 carbons having a linear or branched structure.

The polyethylene glycols, polyethylene oxides, polyethylene glycol monoesters, and polyethylene oxide monoesters may have a number-average molecular weight ranging from 100 to 20000.

The hydroxyl group-containing compound is preferably added to the culture medium for cultivation of the microorganism at a concentration preferably from 0.01 to 10% (w/v), more preferably from 0.02 to 5%(w/v). The compound may be added in one batch in the initial stage of the cultivation, or portionwise during the cultivation period.

The microorganism employed in the present invention is the one which has, as described above, capability of producing a polyhydroxyalkanoate containing at least one of 3-hydroxy-ω-substituted alkanoic acid units represented by Chemical Formula (1), and a 3-hydroxy-ω-cyclohexylalkanoic acid unit represented by Chemical Formula (2), from an ω-substituted alkanoic acid, as the source material, represented by Chemical Formula (3), or an ω-cyclohexylalkanoic acid represented by Chemical Formula (4).

The polyhydroxyalkanoate of the present invention contains at least one of 3-hydroxy-ω-substituted-alkanoic acid units represented by Chemical Formula (16):

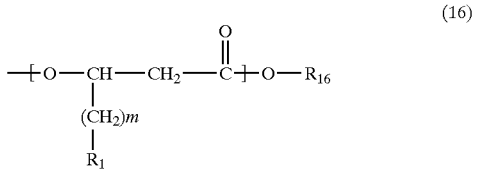

m = 1–8

(in the above formula, m is an integer selected from the numerical range shown with the Chemical Formula; $R_1$ is defined in above and preferably a residue selected from the group consisting of Chemical formulae (5) to (15); in the presence of plural units, m and $R_1$ are selected independently for the respective units; and $R_{16}$ is a group derived from a chemical species selected from the group consisting of alcohols, diols, triols, alkylene glycols, polyethylene glycols, polyethylene oxides, alkylene glycol monoesters, polyethylene glycol monoesters, and polyethylene oxide monoesters); and 3-hydroxy-ω-cyclohexylalkanoic acid units represented by General formula (17):

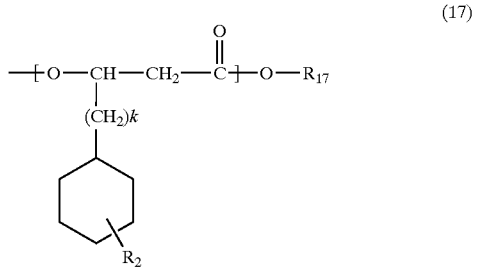

k = 0–8

(in the above formula, $R_2$ denotes a substituent on the cyclohexyl group selected from the group consisting of H atom, CN, $NO_2$, halogen atom, $CH_3$, $C_2H_5$, $C_3H_7$, $CF_3$, $C_2F_5$ and $C_3F_7$; k is an integer selected from the numerical range shown with the Chemical Formula; in the presence of plural units, k and $R_2$ are selected independently for the respective units; and $R_{17}$ is a group derived from a chemical species selected from the group consisting of alcohols, diols, triols, alkylene glycols, polyethylene glycols, polyethylene oxides, alkylene glycol monoesters, polyethylene glycol monoesters, and polyethylene oxide monoesters).

The use of the aforementioned microorganism is the essential constitutional requirement of the present invention. Specifically, the microorganisms employed in U.S. Pat. No. 6,156,852, Biotechnology and Bioengineering, 62, 106–113 (1999), and International Journal of Biological Macromolecules, 25, 43–53 (1999) do not have capability of producing the polyhydroxyalkanoate containing one or more of the units represented by Chemical Formula (1) or (2) starting from the compound represented by Chemical Formula (3) or (4)

The microorganisms shown in the above Japanese Patent Publication and the technical literature are reported to produce usually homopolymers and copolymers of poly 3-hydroxybutyric acid (hereinafter referred to as "PHB"), or poly 3-hydroxyvaleric acid (hereinafter referred to as "PHV"). Typically, the biosynthesis pathway for the PHB is summarized as below:

(1) Acetyl-CoA→Acetoacetyl-CoA (2) Acetoacetyl-CoA→3-hydroxybutyryl-CoA (3) 3-Hydroxybutyryl-CoA→poly 3-hydroxybutric acid.

On the other hand, the microorganism employed in the present invention biosynthesizes a polyhydroxyalkanoate containing one or more of the units represented by Chemical Formula (1) and (2) by taking the compound of Chemical Formula (3) or (4) into the fatty acid degradation pathway called "β-oxidation pathway" by conversion as shown below:

<1> Compound (2)→Acyl-CoA

<2> Acyl-CoA→Enoyl-CoA

<3> Enoyl-CoA→3-Hydorxyacyl-CoA

<4> 3-Hydroxyacyl-CoA→Polyhydroxyalkanoate of Chemical Formula (1).

The enzyme participating directly in the above step (3) is a PHB synthase or a short-chain-length PHA synthase, whereas the enzyme employed in the step <4> of the present invention is a PHA synthase or a medium-chain-length PHA synthase. The both enzymes are different from each other in the substrate specificity. This is shown in detail in review papers such as FEMS microbiology Reviews, 103, 217–230 (1992), and Journal of Biotechnology, 65, 127–161 (1998).

In other words, the microorganism employed in the present invention is completely different from the microorganisms employed in the aforementioned U.S. Pat. No. 6,156,852; Biotechnology and Bioengineering, 62 106–113 (1999); and International Journal of Biological Micromolecules, 25, 43–53 (1999) cited above under the heading of Related Background Art in this Patent Specification.

The microorganism employed in the method of the present invention is not limited, provided that the microorganism has capability of producing the polyhydroxyalkanoate containing at least one of the units represented by Chemical Formula (1) or (2) in the molecule from a source compound represented by Chemical Formula (3) or (4). Among them, particularly preferred are microorganisms of Pseudomonas genus, including specifically *Pseudomonas* cichorii, Pseudomonas putida, Pseudomonas fluorescence, Pseudomonas oleovorans, Pseudomonas aeruginosa, Pseudomonas stutzeri, Peudomonas jessenii, and so forth. More specifically, particularly preferred are Pseudomonas cichori YN2 (FERM BP-7375), Pseudomonas cichorii H45 (FREM BP-7374), Pseudomonas jessenii P161 (FERM BP-7376), and Pseudomonas putida P91 (FREM BP-7373). These four microorganisms have been deposited to International Patent Organism Depositary, National Institute of Advanced Industrial Science and Technology (formerly, National Institute of Bioscience and Human-Technology, Agency of Industrial Science and Technology), and are described in Japanese Patent Application Laid-Open No. 2001-371863.

The microorganism cultivating conditions in the present invention are described below.

Necessary substrate and nutrients are added as explained below to an inorganic culture medium basically constituted of a phosphate buffer, and an ammonium or nitrate salt.

As the substrate for production of the intended polyhydroxyalkanoate, the culture medium contains the compound of Chemical Formula (2) preferably at a content ranging from 0.01 to 1%(w/v), more preferably from 0.02 to 0.2%(w/v).

Usually the culture medium contains preferably the coexisting substrate below as the carbon source and nitrogen source for the microorganism growth, and energy source for the polyalkanoate production at a concentration ranging preferably from 0.1 to 5%(w/v), more preferably from 0.2 to 2%.

Coexisting Substrate:

Natural Culture Component: yeast extract, meat extract, malt extract, kazaminic acid, casein hydrolyzate, polypeptone, trypton, peptone, etc.;

Sugars: aldoses such as glyceroaldehyde, erythrose, arabinose, xylose, glucose, galactose, mannose, and fructose; alditol such as glycerol, erythritol and xylitol; aldonic acids such as gluconic acid; uronic acids such as glucuronic acid and galacturonic acid; disaccharides such as maltose, sucrose and lactose;

Organic acids and salts thereof: pyruvic acid, malic acid, lactic acid, citric acid, succinic acid, oxaloacetic acid, isocitric acid, ketoglutaric acid and fumaric acid, and salts thereof;

Amino acids: glutamic acid, aspartic acid, and salts thereof, etc.;

Alkanoic acids: linear or branched alkanoic acids of 4–12 carbons, etc.

In the present invention, any inorganic culture medium is useful which contains a phosphate salt and a nitrogen source such as an ammonium or nitrate salt. The productivity of PHA can be improved by controlling the concentration of the nitrogen source.

The cultivating temperature is controlled to be suitable for the growth of the aforementioned microorganism strain, ranging preferably from 15° C. to 37° C., more preferably from 20° C. to 30° C.

Any cultivation method may be employed which allows growth of the microorganism to produce PHA, including liquid cultivation and solid cultivation production. The cultivation may be conducted by any kind of cultivation process such as batch cultivation, fed-batch cultivation, semi-continuous cultivation and continuous cultivation. The liquid cultivation method includes a flask-shaking method for oxygen supply, and stirring aeration with a jar fermentor for oxygen supply.

In another method for producing and accumulating the PHA in the microorganism, the microorganism is allowed to grow sufficiently, then the microorganism mass is transferred to a separate culture medium containing a limited amount of a nitrogen source like ammonium chloride, and the cultivation is continued with addition of the compound for the substrate of the intended units to improve the productivity possibly.

The objective PHA can be isolated from the microorganism cells after cultivation as described above in a conventional process in the present invention. For example, the most simplest process is extraction with an organic solvent like chloroform, dichloromethane, and acetone. Another organic solvent such as dioxane, tetrahydrofuran and acetonitrile can be useful. In the environment in which use of the organic solvent is not suitable, PHA can be recovered by physically crushing the microorganism cells to remove the cell component other than PHA by any of the methods: treatment with a surfactant like SDS; treatment with an enzyme like lysozyme; by treatment with a chemical such as hypochlorite salts, ammonia and EDTA; and physical crushing of the microorganism cells by ultrasonic crushing, homogenizer crushing, pressure crushing, bead-impact crushing, milling, grinding, and freeze-melting.

Incidentally, in the present invention, the methods are not limited to the above for cultivation of the microorganism, production and accumulation of PHA in the microorganism cells, and the recovery of PHA by removal of the microorganism cell components other than PHA.

As shown in the following working examples, the method of the resent invention enables control of the molecular weight of polyhydroxyalkanoate which contains a unit having a residue containing a phenyl-, thienyl-, or cyclohexyl-structure in the side chain of the molecule.

DESCRIPTION OF THE PREFERRED EMBODIMENT

The composition of the inorganic salt culture medium (M9 culture medium) which was used in a method of the present invention is shown below.

| <M9 Culture Medium> | | |
|---|---|---|
| $Na_2HPO_4$: | 6.3 | |
| $KH_2PO_4$: | 3.0 | |
| $NH_4Cl$: | 1.0 | |
| $NaCl$: | 0.5 | g/L, pH = 7.0 |

For more effective cell growth and PHS production, the minor component solutions should be added to the culture medium in an amount of about 0.3%(v/v) as shown below.

Minor Component Solution

Nitrilotriacetic Acid:1.5; $MgSO_4$:3.0; $MnSO_4$:0.5; NaCl:1.0; $FeSO_4$:0.1; $CaCl_2$:0.1; $CoCl_2$:0.1; $ZnSO_4$:0.1; $CuSO_4$:0.1; $AlK(SO_4)_2$:0.1; $H_3BO_3$:0.1; $Na_2MoO_4$:0.1; $NiCl_2$:0.1 (g/L)

EXAMPLES

Example 1

Molecular Weight Control (1) of Poly 3-hydroxy-5-phenylvaleric Acid (PHPV) by Polyethylene Glycol:

Pseudomonas cichorii YN2 strain was cultivated in an M9 culture medium containing 0.5% of polypeptone at 30° C. for 8 hours with shaking. A 1-mL portion of this liquid culture was added to 200-mL portions of an M9 culture medium respectively containing 0.5%(w/v) of polypeptone (Wako Junnyaku K. K.), 0.1%(w/v) of 5-phenylvaleric acid, and 0%, 1%, 2%, or 5%(v/v) of polyethylene glycol 200 (PEG200: average molecular weight 190–210; Kishida Kagaku K. K.) as the molecular weight controlling agent, and cultivated at 30° C. for 24 hour in a 500-mL shaking flask. After the cultivation, the microorganism mass was recovered by centrifugation, washed with methanol, and freeze-dried. The dried microorganism mass, after weighing, was stirred in chloroform at 50° C. for 24 hours to extract the polymer. The chloroform containing the extracted polymer was filtered and was concentrated by an evaporator. Then cold methanol was added thereto, and solid precipitation formed by addition of the methanol was collected and vacuum-dried to obtain the intended polymer.

The obtained polymer was subjected to polymer structure determination by $^1$H-NMR (FT-NMR: Bruker DPX400; $^1$H resonance frequency: 400 MHz; measured nuclear species: $^1$H; solvent used: CDCl$_3$; reference: capillary-sealed TMS/CDCl$_3$; measurement temperature: room temperature). Thereby the respective polymers were found to be composed mainly of a homopolymer of 3-hydroxy-5-phenylvaleric acid (hereinafter referred to as "PHPV") (Chemical Formula (18) below):

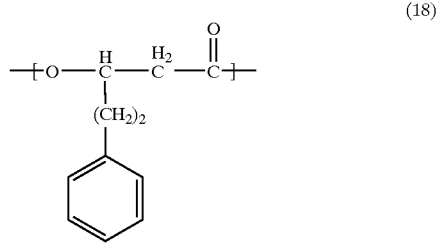

(18)

The molecular weight of the polymer was measured by gel permeation chromatography (GPC) (Tosoh HLC-8220 GPC, column: Tosoh TSK-gel SuperHM-H, solvent: chloroform, polystyrene basis).

Table 1 shows the weight of the obtained microorganism mass, the weight of the obtained polymer, weight ratio of the polymer to the microorganism mass, and the molecular weight and molecular weight distribution of the polymer.

TABLE 1

| PEG200 (%) | CDW(mg/L) | PDW(mg/L) | P/C (%) | Mn | Mw/Mn |
|---|---|---|---|---|---|
| 0 | 1238 | 603 | 48.7 | 92000 | 1.9 |
| 1 | 1022 | 523 | 51.1 | 26000 | 2.0 |
| 2 | 1007 | 513 | 50.9 | 18000 | 2.1 |
| 5 | 625 | 343 | 54.8 | 15000 | 2.1 |

CDW: dry weight of the microorganism mass
PDW: dry weight of the polymer
P/C: PDW/CDW, Mn: number-average molecular weight
Mw/Mn: molecular weight distribution Example 2
Molecular Weight Control (2) of PHPV by Polyethylene Glycol:

The experiment was conducted in the same manner as in Example 1 except that PEG600 (average molecular weight: 570–630) was used in place of PEG200 as the molecular weight-controlling agent. According to $^1$H-NMR analysis, the obtained polymers were found respectively to be composed mainly of a PHPV similarly as in Example 1. Table 2 shows the weight of the obtained microorganism mass, the weight of the obtained polymer, the weight ratio of the polymer to the microroorganism mass, the molecular weight and molecular weight distribution of the polymer.

TABLE 2

| PEG600 (%) | CDW(mg/L) | PDW(mg/L) | P/C (%) | Mn | Mw/Mn |
|---|---|---|---|---|---|
| 0 | 1205 | 600 | 49.8 | 92000 | 1.9 |
| 1 | 1100 | 533 | 48.5 | 70000 | 1.9 |
| 2 | 1090 | 533 | 48.9 | 55000 | 2.1 |
| 5 | 605 | 321 | 53.1 | 49000 | 2.0 |

CDW: dry weight of the microorganism mass
PDW: dry weight of the polymer
P/C: PDW/CDW, Mn: number-average molecular weight
Mw/Mn: molecular weight distribution Example 3

Molecular Weight Control (3) of PHPV by Polyethylene Glycol:

The experiment was conducted in the same manner as in Example 1 except that PEG2000 (average molecular weight: 1800–2200) was used in place of PEG200 as the molecular weight-controlling agent. According to $^1$H-NMR analysis, the obtained polymers were found respectively to be composed mainly of a PHPV similarly as in Example 1. Table 3 shows the weight of the obtained microorganism mass, the weight of the obtained polymer, the weight ratio of the polymer to the microorganism mass, and the molecular weight and molecular weight distribution of the polymer.

TABLE 3

| PEG2000 (%) | CDW(mg/L) | PDW(mg/L) | P/C (%) | Mn | Mw/Mn |
|---|---|---|---|---|---|
| 0 | 1225 | 602 | 49.1 | 92000 | 1.9 |
| 1 | 1090 | 519 | 47.6 | 80000 | 2.1 |
| 2 | 1070 | 522 | 48.8 | 67000 | 2.0 |
| 5 | 618 | 320 | 51.8 | 61000 | 1.9 |

CDW: dry weight of the microorganism mass
PDW: dry weight of the polymer
P/C: PDW/CDW, Mn: number-average molecular weight
Mw/Mn: molecular weight distribution Example 4

Molecular Weight Control of Poly 3-hydroxy-5-phenoxyvaleric Acid by Polyethylene Glycol:

Pseudomonas cichorii YN2 strain, and Pseudomonas putida P161 strain were separately cultivated in an M9 culture medium containing 0.5% of polypeptone at 30° C. for 8 hours with shaking. A 1-mL portion of one of the liquid cultures was added to a 200-ml portion of an M9 culture medium containing 0.5%(w/v) of polypeptone and 0.1%(w/v) of 5-phenoxyvaleric acid, and containing no PEG200 or containing 1%(v/v) of PEG200 as the molecular weight-controlling agent. Cultivation was conducted at 30° C. for 45 hours in a 500-mL shaking flask. After the cultivation, the intended polymer was obtained in the same manner as in Example 1.

According to $^1$H-NMR analysis, the obtained polymers were found to be composed mainly of a homopolymer of 3-hydroxy-5-phenoxyvaleric acid (Chemical Formula (19) below):

(19)

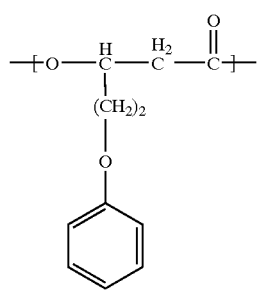

The molecular weight of the polymer was measured by GPC in the same manner as in Example 1.

Table 4 shows the weight of the obtained microorganism mass, the weight of the obtained polymer, the weight ratio of the polymer to the microorganism mass, and the molecular weight and molecular weight distribution of the polymer.

TABLE 4

| Micro-organism | PEG200: 1% | CDW (mg/L) | PDW (mg/L) | P/C (%) | Mn | Mw/Mn |
|---|---|---|---|---|---|---|
| YN2 | None | 760 | 360 | 47.4 | 225000 | 2.1 |
|  | Contained | 750 | 175 | 23.3 | 92000 | 2.0 |
| P161 | None | 680 | 150 | 22.1 | 160000 | 1.9 |
|  | Contained | 530 | 40 | 7.5 | 40000 | 2.0 |

CDW: dry weight of the microorganism mass
PDW: dry weight of the polymer
P/C: PDW/CDW, Mn: number-average molecular weight
Mw/Mn: molecular weight distribution Example 5

Molecular Weight Control of PHPV by Various Molecular Weight-Controlling Agents:

Pseudomonas cichorii YN2 strain was cultivated in an M9 culture medium containing 0.5% of polypeptone at 30° C. for 8 hours with shaking. A 1-mL portion of this liquid culture was added to 200-mL portions of an M9 culture medium respectively containing 0.5%(w/v) of polypeptone and 0.1%(w/v) of 5-phenylvaleric acid, and containing no molecular weight-controlling agent or containing 0.1%(v/v) of PEG200 or isopropanol (Kishida Kagaku K. K.) or n-butanol (Kishida Kagaku K. K.) as the molecular weight-controlling agent. Cultivation was conducted at 30° C. for 40 hours in a 500-mL shaking flask. After the cultivation, the intended polymers were obtained in the same manner as in Example 1.

According to $^1$H-NMR analysis, the obtained polymers were found to be composed mainly of a homopolymer of PHPV.

The molecular weight of the polymer was measured by GPC in the same manner as in Example 1.

Table 5 shows the weight of the obtained microorganism mass, the weight of the obtained polymer, the weight ratio of the polymer to the microorganism mass, and the molecular weight and molecular weight distribution of the polymer.

TABLE 5

| MW controlling agent | CDW (mg/L) | PDW (mg/L) | P/C (%) | Mn | Mw/Mn |
|---|---|---|---|---|---|
| None | 1170 | 705 | 60.3 | 94000 | 1.9 |
| PEG200 | 1100 | 540 | 49.1 | 65000 | 2.1 |

TABLE 5-continued

| MW controlling agent | CDW (mg/L) | PDW (mg/L) | P/C (%) | Mn | Mw/Mn |
|---|---|---|---|---|---|
| IPA | 1210 | 600 | 49.6 | 79000 | 1.9 |
| BA | 1470 | 635 | 43.2 | 36000 | 2.3 |

CDW: dry weight of the microorganism mass
PDW: dry weight of the polymer
P/C: PDW/CDW, Mn: number-average molecular weight
Mw/Mn: molecular weight distribution
IPA: isopropanol, BA: n-butanol Example 6

Molecular Weight Control of Poly 3-hydroxy-5-(phenylsulfanyl)valeric Acid by Various Molecular Weight-Controlling Agents:

Pseudomonas cichorii YN2 strain was cultivated in an M9 culture medium containing 0.5% of polypeptone at 30° C. for 8 hours with shaking. A 1-mL portion of this liquid culture was added to 200-mL portions of an M9 culture medium respectively containing 0.5% of polypeptone, 0.1% of 5-(phenylsufanyl)valeric acid, and containing no molecular weight-controlling agent or containing 0.1%(v/v) of 1,2-butanediol, 1,4-butanediol, 1,6-hexanediol, 1,2,3-butanetriol, ethylene glycol, or ethylene glycol momoethyl ether as the molecular weight-controlling agent. Cutivation was conducted at 30° C. for 48 hours in a 500-mL shaking flask. After the cultivation, the intended polymers were obtained in the same manner as in Example 1.

According to $^1$H-NMR analysis, the obtained polymers were found to be composed mainly of a homopolymer of 3-hydroxy-5-(phenylsulfanyl)valeric acid (Chemical Formula (20) below).

(20)

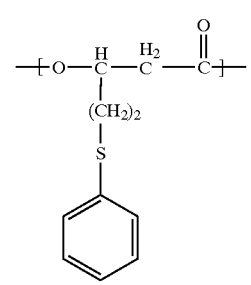

The molecular weight of the polymer was measured by GPC in the same manner as in Example 1.

Table 6 shows the weight of the obtained microorganism mass, the weight of the obtained polymer, the weight ratio of the polymer to the microorganism mass, and the molecular weight and molecular weight distribution of the polymer.

TABLE 6

| MW controlling agent | CDW (mg/L) | PDW (mg/L) | P/C (%) | Mn | Mw/Mn |
|---|---|---|---|---|---|
| None | 1210 | 590 | 48.8 | 150000 | 2.3 |
| 1,2-BD | 1200 | 570 | 47.5 | 42000 | 2.2 |
| 1,3-BD | 1215 | 565 | 46.5 | 44000 | 2.1 |

TABLE 6-continued

| MW controlling agent | CDW (mg/L) | PDW (mg/L) | P/C (%) | Mn | Mw/Mn |
|---|---|---|---|---|---|
| 1,6-HD | 1150 | 575 | 50.0 | 29000 | 2.1 |
| 1,2,3-BT | 1090 | 505 | 46.3 | 45000 | 2.3 |
| EG | 1230 | 600 | 48.8 | 50000 | 2.2 |
| MEG | 1200 | 590 | 49.2 | 53000 | 2.2 |

CDW: dry weight of the microorganism mass
PDW: dry weight of the polymer
P/C: PDW/CDW, Mn: number-average molecular weight
Mw/Mn: molecular weight distribution
1,2-BD: 1,2-butanediol; 1,4-BD: 1,4-butanediol; 1,6-HD: 1,6-hexanediol; 1,2,3-BT: 1,2,3-butanetriol; EG: ethylene glycol; MEG: ethylene glycol monomethyl ether Example 7
Molecular Weight Control of Poly 3-hydroxy-5-(2-thienyl) valeric Acid by PEG:

*Pseudomonas putida* P91 strain was cultivated in an M9 culture medium containing 0.5% of a yeast extract (Difco) at 30° C. for 8 hours with shaking. A 1-mL portion of this liquid culture was added to 200-mL portions of an M9 culture medium containing respectively 0.5% of the yeast extract, 0.1% of 5-(2-thienyl)valeric acid, and containing no molecular weight-controlling agent or containing 0.1%(v/v) of PEG200 as the molecular weight-controlling agent. Cultivation was conducted at 30° C. for 45 hours in a 500-mL shaking flask. After the cultivation, the intended polymers were obtained in the same manner as in Example 1.

According to $^1$H-NMR analysis, the obtained polymers were found to be composed mainly of a homopolymer of 3-hydroxy-5-(2-thienyl)valeric acid (Chemical Formula (21) below).

(21)

$$\text{-}\!\!\left[\!\text{O}\!-\!\overset{H}{\underset{(CH_2)_2}{C}}\!-\!\overset{H_2}{C}\!-\!\overset{O}{\overset{\|}{C}}\!\right]\!\text{-}$$

(with thienyl group)

The molecular weight of the polymer was measured by GPC in the same manner as in Example 1.

Table 7 shows the weight of the obtained microorganism mass, the weight of the polymer, the weight ratio of the polymer to the microorganism mass, and the molecular weight and molecular weight distribution of the polymer.

TABLE 7

| PEG200: 1% | CDW (mg/L) | PDW (mg/L) | P/C (%) | Mn | Mw/Mn |
|---|---|---|---|---|---|
| None | 600 | 15 | 2.5 | 72000 | 3.2 |
| Contained | 540 | 16 | 3.0 | 30000 | 2.8 |

CDW: dry weight of the microorganism mass
PDW: dry weight of the polymer
P/C: PDW/CDW, Mn: number-average molecular weight
Mw/Mn: molecular weight distribution Example 8
Molecular Weight Control of Poly 3-hydroxy-5-(4-fluorophenyl)valeric Acid by PEG:

*Pseudomonas cichorii* YN2 strain was cultivated in an M9 culture medium containing 0.5% of polypeptone at 30° C. for 8 hours with shaking. A 1-mL portion of this liquid culture was added to 200-mL portions of an M9 culture medium respectively containing 0.5% of D-glucose (Kishida Kagaku K. K.), 0.1% of 5-(4-fluorophenyl)valeric acid, and containing no PEG200 or containing 1%(v/v) of PEG200 as the molecular weight-controlling agent. Cultivation was conducted at 30° C. for 48 hours in a 500-mL shaking flask. After the cultivation, the intended polymers were obtained in the same manner as in Example 1.

According to $^1$H-NMR analysis, the obtained polymers were found to be composed mainly of a homopolymer of 3-hydroxy-5-(4-fluorophenyl)valeric acid (Chemical Formula (22) below).

(22)

$$\text{-}\!\!\left[\!\text{O}\!-\!\overset{H}{\underset{(CH_2)_2}{C}}\!-\!\overset{H_2}{C}\!-\!\overset{O}{\overset{\|}{C}}\!\right]\!\text{-}$$

(with 4-fluorophenyl group)

The molecular weight of the polymer was measured by GPC in the same manner as in Example 1.

Table 8 shows the weight of the obtained microorganism mass, the weight of the polymer, the weight ratio of the polymer to the microorganism mass, and the molecular weight and molecular weight distribution of the polymer.

TABLE 8

| PEG200: 1% | CDW (mg/L) | PDW (mg/L) | P/C (%) | Mn | Mw/Mn |
|---|---|---|---|---|---|
| None | 790 | 430 | 54.4 | 90000 | 2.1 |
| Contained | 700 | 390 | 55.7 | 22000 | 2.0 |

CDW: dry weight of the microorganism mass
PDW: dry weight of the polymer
P/C: PDW/CDW, Mn: number-average molecular weight
Mw/Mn: molecular weight distribution Example 9
Molecular Weight Control of Poly 3-hydroxy-4-phenylbutyric Acid and Poly 3-hydroxy-6-phenylhexanoic Acid by PEG:

The molecular weight-controlling effect of PEG200 was evaluated in the same manner as in Example 8 except that the polymer synthesis substrate was changed to 4-phenylbutyric acid, or 6-phenylhexanoic acid.

According to $^1$H-NMR analysis, the obtained polymers were found to be composed mainly of a homopolymer of 3-hydroxy-4-phenylbutyric acid (Chemical Formula (23) below) or a homopolymer of 3-hydroxy-6-phenylhexanoic acid (Chemical Formula (24) below).

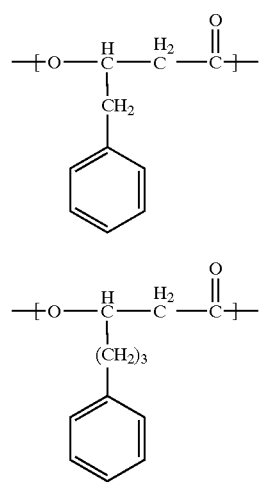

(23)

(24)

The molecular weight of the polymer was measured by GPC in the same manner as in Example 1.

Table 9 shows the weight of the obtained microorganism mass, the weight of the polymer, the weight ratio of the polymer to the microorganism mass, and the molecular weight and molecular weight distribution of the polymer.

TABLE 9

| Polymer | PEG200: 1% | CDW (mg/L) | PDW (mg/L) | P/C (%) | Mn | Mw/Mn |
|---|---|---|---|---|---|---|
| PHPB | None | 420 | 66 | 15.7 | 78000 | 2.2 |
|  | Contained | 420 | 69 | 16.4 | 19000 | 2.1 |
| PHPHx | None | 700 | 72 | 10.3 | 80000 | 2.3 |
|  | Contained | 660 | 69 | 10.5 | 23000 | 2.1 |

PHPB: poly 3-hydroxy-4-phenylbutyric acid
PHPHx: poly 3-hydroxy-6-phenylhexanoic acid
CDW: dry weight of the microorganism mass
PDW: dry weight of the polymer
P/C: PDW/CDW, Mn: number-average molecular weight
Mw/Mn: molecular weight distribution Example 10

Molecular Weight Control of Poly 3-hydroxy-4-cyclohexylbutyric Acid by PEG:

The molecular weight-controlling effect of PEG200 was evaluated in the same manner as in Example 8 except that the growth substrate was changed from D-glucose to polypeptone.

According to $^1$H-NMR analysis, the obtained polymers were found to be composed mainly of a homopolymer of 3-hydroxy-4-cyclohexylbutyric acid (Chemical Formula (25) below).

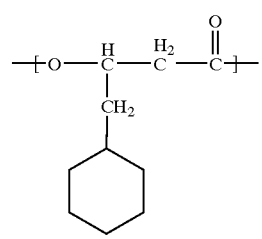

(25)

The molecular weight of the polymer was measured by GPC in the same manner as in Example 1.

Table 10 shows the weight of the obtained microorganism mass, the weight of the polymer, the weight ratio of the polymer to the microorganism mass, and the molecular weight and molecular weight distribution of the polymer.

TABLE 10

| PEG200: 1% | CDW (mg/L) | PDW (mg/L) | P/C (%) | Mn | Mw/Mn |
|---|---|---|---|---|---|
| None | 820 | 480 | 58.5 | 71000 | 2.2 |
| Contained | 820 | 430 | 52.4 | 18000 | 2.1 |

CDW: dry weight of the microorganism mass
PDW: dry weight of the polymer
P/C: PDW/CDW, Mn: number-average molecular weight
Mw/Mn: molecular weight distribution Example 11

Molecular Weight Control of PHA Containing 3-Hydroxy-5-phenoxyvaleric Acid Unit and 3-Hydroxy-5-(4-cyanophenoxy)valeric Acid Unit by PEG:

*Pseudomonas cichorii* YN2 strain was cultivated in an M9 culture medium containing 0.5% of polypeptone at 30° C. for 8 hours with shaking. A 1-mL portion of this liquid culture was added to 200-mL portions of an M9 culture medium containing 0.5% of polypeptone, 0.05% of 5-(4-cyanophenoxy)valeric acid, and 0.05% of 5-phenoxyvaleric acid, and containing no molecular weight-controlling agent or containing 1%(v/v) of PEG200 as the molecular weight-controlling agent. Cultivation was conducted at 30° C. for 48 hours in a 500-mL shaking flask. After the cultivation, the intended polymers were obtained by purification in the same manner as in Example 1 and recovery of an acetone-soluble component only.

According to $^1$H-NMR analysis, the obtained polymers were found to be a PHA containing the units of 3-hydroxy-5-phnoxyvaleric acid and 3-hydroxy-5-(4-cyanophenoxy)valeric acid shown by Chemical Formula (26) below, in which the unit ratio of A:B:C:D=2:25:5:68 (no PEG-containing medium) and 3:24:7:66 (PEG-containing medium).

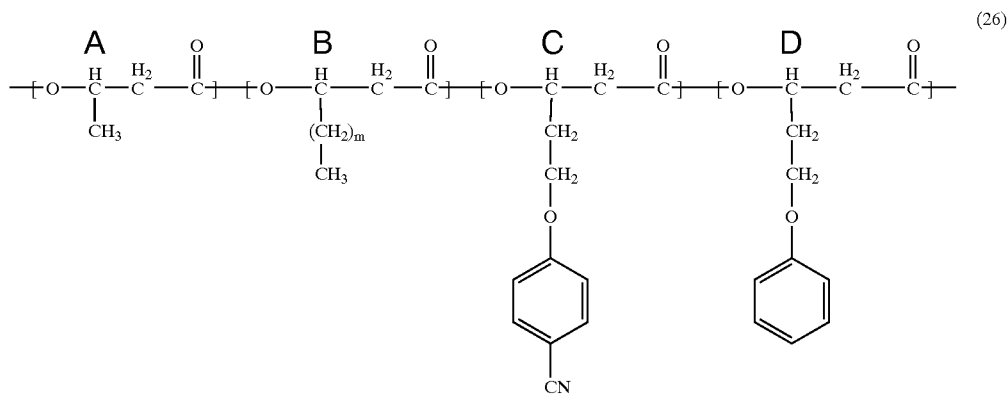

(26)

The molecular weight of the polymer was measured by GPC in the same manner as in Example 1.

Table 11 shows the weight of the obtained microorganism mass, the weight of the polymer, the weight ratio of the polymer to the microorganism mass, and the molecular weight and molecular weight distribution of the polymer.

TABLE 11

| PEG200: 1% | CDW (mg/L) | PDW (mg/L) | P/C (%) | Mn | Mw/Mn |
|---|---|---|---|---|---|
| None | 680 | 110 | 16.2 | 72000 | 2.3 |
| Contained | 660 | 100 | 15.2 | 20000 | 2.1 |

CDW: dry weight of the microorganism mass
PDW: dry weight of the polymer
P/C: PDW/CDW, Mn: number-average molecular weight
Mw/Mn: molecular weight distribution

Example 12
Molecular Weight Control of PHA Containing 3-Hydroxy-5-phenoxyvaleric Acid Unit and 3-Hydroxy-5-(4-nitrophenoxy)valeric Acid Unit by PEG:

The molecular weight-controlling effect of PEG was evaluated by producing a polymer in the same manner as in Example 11 except that 5-(4-cyanophenoxy)valeric acid in the polymer producing substrate was changed to 5-(4-nitrophenoxy)valeric acid.

According to $^1$H-NMR analysis, the obtained polymers were found respectively to be a PHA containing the units of 3-hydroxy-5-phnoxyvaleric acid and 3-hydroxy-5-(4-nitrophenoxy)valeric acid shown by Chemical Formula (27) below, in which the unit ratio of A:B:C:D=2:22:4:72 (no PEG-containing medium) and 4:23:5:68 (PEG-containing medium).

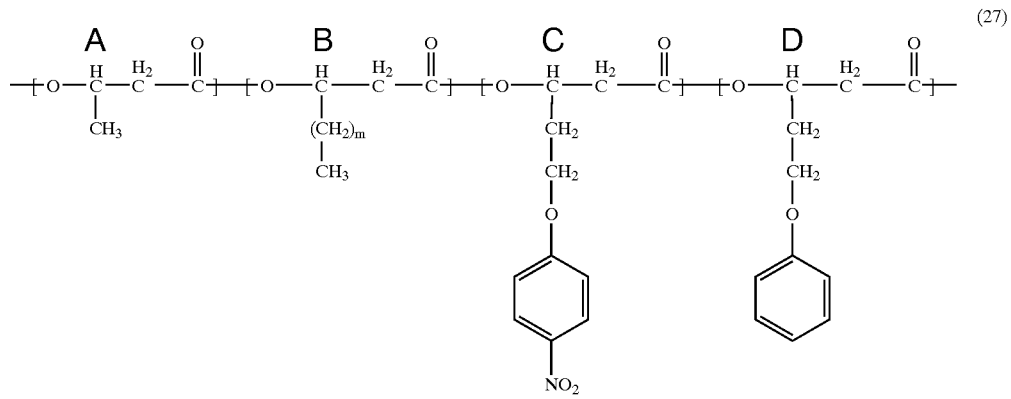

(27)

The molecular weight of the polymer was measured by GPC in the same manner as in Example 1.

Table 12 shows the weight of the obtained microorganism mass, the weight of the polymer, the weight ratio of the polymer to the microorganism mass, and the molecular weight and molecular weight distribution of the polymer.

TABLE 12

| PEG200: 1% | CDW (mg/L) | PDW (mg/L) | P/C (%) | Mn | Mw/Mn |
|---|---|---|---|---|---|
| None | 590 | 95 | 16.1 | 70000 | 2.2 |
| Contained | 570 | 80 | 14.0 | 17000 | 2.1 |

CDW: dry weight of the microorganism mass
PDW: dry weight of the polymer
P/C: PDW/CDW, Mn: number-average molecular weight
Mw/Mn: molecular weight distribution

Example 13

Molecular Weight Control of PHA Containing Units of 3-Hydroxy-5-phenoxyvaleric Acid, 3-Hydroxy-7-phenoxyheptanoic Acid, and 3-Hydroxy-9-phenoxynonanoic Acid by PEG:

The molecular weight-controlling effect of PEG was evaluated by producing a polymer in the same manner as in Example 10 except that 11-phenoxyundecanoic acid was used as the polymer synthesizing substrate, and *Pseudomonas cichorii* H45 strain was employed as the production strain.

According to $^1$H-NMR analysis, the obtained polymers were found respectively to be a PHA containing the units of 3-hydroxy-5-phnoxyvaleric acid, 3-hydroxy-7-phenoxyheptanoic acid, and 3-hydroxy-9-phenoxynonanoic acid shown by Chemical Formula (28) below, in which the unit ratio of A:B:C:D:E=3:1:34:51:11 (no PEG-containing medium) and 3:1:35:52:9 (PEG-containing medium).

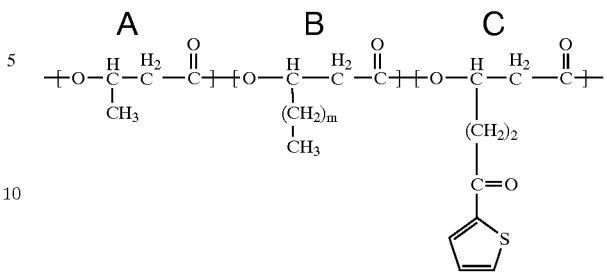

(29)

The molecular weight of the polymer was measured by GPC in the same manner as in Example 1.

Table 14 shows the weight of the obtained microorganism mass, the weight of the polymer, the weight ratio of the

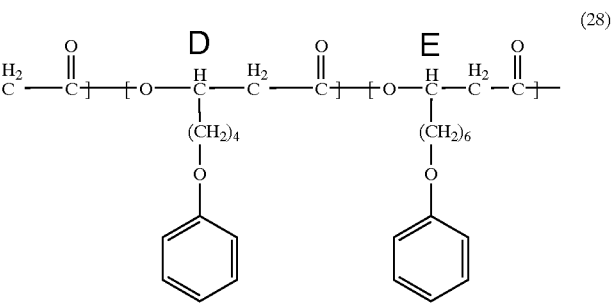

(28)

The molecular weight of the polymer was measured by GPC in the same manner as in Example 1.

Table 13 shows the weight of the obtained microorganism mass, the weight of the polymer, the weight ratio of the polymer to the microorganism mass, and the molecular weight and molecular weight distribution of the polymer.

TABLE 13

| PEG200: 1% | CDW (mg/L) | PDW (mg/L) | P/C (%) | Mn | Mw/Mn |
|---|---|---|---|---|---|
| None | 820 | 290 | 35.4 | 33000 | 1.9 |
| Contained | 815 | 280 | 34.4 | 10000 | 1.9 |

CDW: dry weight of the microorganism mass
PDW: dry weight of the polymer
P/C: PDW/CDW, Mn: number-average molecular weight
Mw/Mn: molecular weight distribution

Example 14

Molecular Weight Control of PHA Containing 3-Hydroxy-5-(2-thienoyl)valeric Acid Unit by PEG:

The molecular weight-controlling effect of PEG was evaluated by producing a polymer in the same manner as in Example 8 except that 5-(2-thienoyl)valeric acid was used as the polymer-synthesizing substrate.

According to $^1$H-NMR analysis, the obtained polymers were found respectively to be a PHA containing a 3-hydroxy-5-(2-thienoyl)valeric acid unit shown by. Chemical Formula (29) below, in which the unit ratio of A:B:C= 1:37:62 (no PEG-containing medium) and 1:35:64 (PEG-containing medium).

polymer to the microorganism mass, and the molecular weight and molecular weight distribution of the polymer.

TABLE 14

| PEG200: 1% | CDW (mg/L) | PDW (mg/L) | P/C (%) | Mn | Mw/Mn |
|---|---|---|---|---|---|
| None | 870 | 95 | 10.9 | 110000 | 2.4 |
| Contained | 875 | 100 | 11.4 | 45000 | 2.2 |

CDW: dry weight of the microorganism mass
PDW: dry weight of the polymer
P/C: PDW/CDW, Mn: number-average molecular weight
Mw/Mn: molecular weight distribution

Example 15

Molecular Weight Control of PHA Containing 3-Hydroxy-5-benzoylvaleric Acid Unit by PEG:

The molecular weight-controlling effect of PEG was evaluated by producing a polymer in the same manner as in Example 8 except that 5-benzoylvaleric acid was used as the polymer-synthesizing substrate.

According to $^1$H-NMR analysis, the obtained polymers were found respectively to be a PHA containing a 3-hydroxy-5-benzoylvaleric acid unit shown by Chemical Formula (30) below, in which the unit ratio of A:B=16:84 (no PEG-containing medium) and 15:85 (PEG-containing medium).

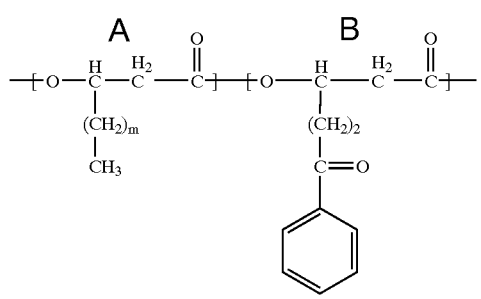

(30)

The molecular weight of the polymer was measured by GPC in the same manner as in Example 1.

Table 15 shows the weight of the obtained microorganism mass, the weight of the polymer, the weight ratio of the polymer to the microorganism mass, and the molecular weight and molecular weight distribution of the polymer.

TABLE 15

| PEG200: 1% | CDW (mg/L) | PDW (mg/L) | P/C (%) | Mn | Mw/Mn |
|---|---|---|---|---|---|
| None | 660 | 170 | 25.8 | 330000 | 3.9 |
| Contained | 665 | 180 | 27.1 | 95000 | 3.7 |

CDW: dry weight of the microorganism mass
PDW: dry weight of the polymer
P/C: PDW/CDW, Mn: number-average molecular weight
Mw/Mn: molecular weight distribution Example 16

Molecular Weight Control of PHA Containing 3-Hydroxy-5-(2-thienylthio)valeric Acid Unit by PEG:

The molecular weight-controlling effect of PEG was evaluated by producing a polymer in the same manner as in Example 11 except that 5-(2-thienylthio)valeric acid was used as the polymer-synthesizing substrate.

According to $^1$H-NMR analysis, the obtained polymers were found to be composed mainly of a homopolymer of 3-hydroxy-5-(2-thienylthio)valeric acid shown by Chemical Formula (31) below.

(31)

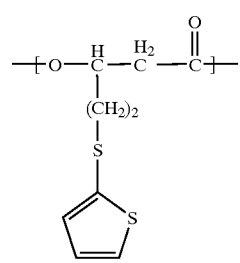

The molecular weight of the polymer was measured by GPC in the same manner as in Example 1.

Table 16 shows the weight of the obtained microorganism mass, the weight of the polymer, the weight ratio of the polymer to the microorganism mass, and the molecular weight and molecular weight distribution of the polymer.

TABLE 16

| PEG200: 1% | CDW (mg/L) | PDW (mg/L) | P/C (%) | Mn | Mw/Mn |
|---|---|---|---|---|---|
| None | 1100 | 350 | 31.8 | 196000 | 2.9 |
| Contained | 1050 | 350 | 33.3 | 74000 | 2.6 |

CDW: dry weight of the microorganism mass
PDW: dry weight of the polymer
P/C: PDW/CDW, Mn: number-average molecular weight
Mw/Mn: molecular weight distribution Example 17

Molecular Weight Control of PHA Containing 3-Hydroxy-5-[(phenylmethyl)sulfanyl]valeric Acid Unit by PEG:

The molecular weight-controlling effect of PEG was evaluated by producing a polymer in the same manner as in Example 8 except that 5-[(phenylmethyl)sulfanyl]valeric acid was used as the polymer-synthesizing substrate.

According to $^1$H-NMR analysis, the obtained polymers were found respectively to be a PHA containing a 3-hydroxy-5-[(phenylmethyl)sulfanyl]valeric acid unit shown by Chemical Formula (32) below, in which the unit ratio of A:B:C=2:8:90 (no PEG-containing medium) and 2:9:89 (PEG-containing medium).

(32)

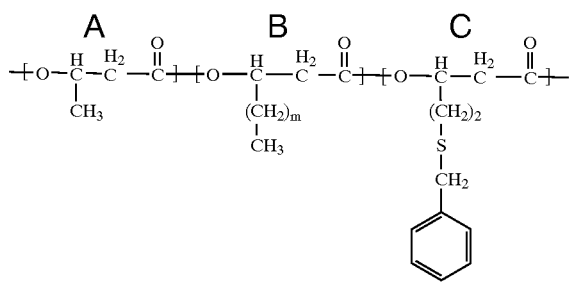

The molecular weight of the polymer was measured by GPC in the same manner as in Example 1.

Table 17 shows the weight of the obtained microorganism mass, the weight of the polymer, the weight ratio of the polymer to the microorganism mass, and the molecular weight and molecular weight distribution of the polymer.

TABLE 17

| PEG200: 1% | CDW (mg/L) | PDW (mg/L) | P/C (%) | Mn | Mw/Mn |
|---|---|---|---|---|---|
| None | 980 | 440 | 44.9 | 15000 | 3.6 |
| Contained | 990 | 400 | 40.4 | 9000 | 3.2 |

CDW: dry weight of the microorganism mass
PDW: dry weight of the polymer
P/C: PDW/CDW, Mn: number-average molecular weight
Mw/Mn: molecular weight distribution Example 18

Molecular Weight Control of PHA Containing 3-Hydroxy-5-phenylvaleric Acid Unit and 3-Hydroxy-5-(4-vinylphenyl)valeric Acid Unit by PEG:

The molecular weight-controlling effect of PEG was evaluated by producing a polymer in the same manner as in Example 10 except that 5-phenylvaleric acid (0.09%) and 5-(4-vinylphenyl)valeric acid (0.02%) were used as the polymer-synthesizing substrates and the chloroform extraction conditions were changed to 23.5° C. and 72 hours.

According to ¹H-NMR analysis, the obtained polymers were found respectively to be a PHA containing a 3-hydroxy-5-phenylvaleric acid unit and a 3-hydroxy-5-(vinylphenyl)valeric acid unit as shown by Chemical Formula (33) below, in which the unit ratio of A:B:C=1:14:85 (no PEG-containing medium) and 1:15:84 (PEG-containing medium).

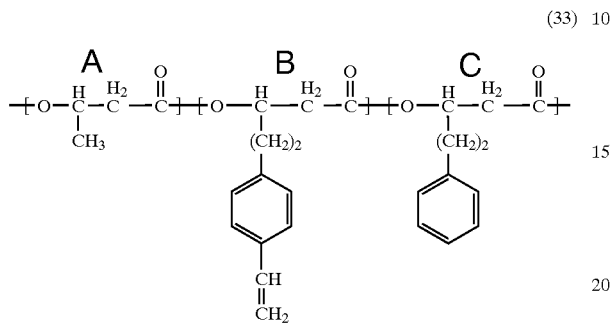

(33)

The molecular weight of the polymer was measured by GPC in the same manner as in Example 1.

Table 18 shows the weight of the obtained microorganism mass, the weight of the polymer, the weight ratio of the polymer to the microorganism mass, and the molecular weight and molecular weight distribution of the polymer.

TABLE 18

| PEG200: 1% | CDW (mg/L) | PDW (mg/L) | P/C (%) | Mn | Mw/Mn |
|---|---|---|---|---|---|
| None | 1200 | 600 | 50.0 | 59000 | 2.0 |
| Contained | 1150 | 580 | 50.4 | 19000 | 1.9 |

CDW: dry weight of the microorganism mass
PDW: dry weight of the polymer
P/C: PDW/CDW, Mn: number-average molecular weight
Mw/Mn: molecular weight distribution Example 19

Molecular Weight Control of PHA Containing 3-Hydroxy-5-[(methylsulfanyl)phenoxy]valeric Acid Unit by PEG:

The molecular weight-controlling effect of PEG was evaluated by producing a polymer in the same manner as in Example 10 except that 5-[(methylsulfanyl)phenoxy]valeric acid was used as the polymer-synthesizing substrate.

According to ¹H-NMR analysis, the obtained polymers were found respectively to be a PHA containing a 3-hydroxy-5-[(methylsulfanyl)phenoxy]valeric acid unit shown by Chemical Formula (34) below, in which the unit ratio of A:B:C=8:68:24 (no PEG-containing medium) and 7:66:27 (PEG-containing medium).

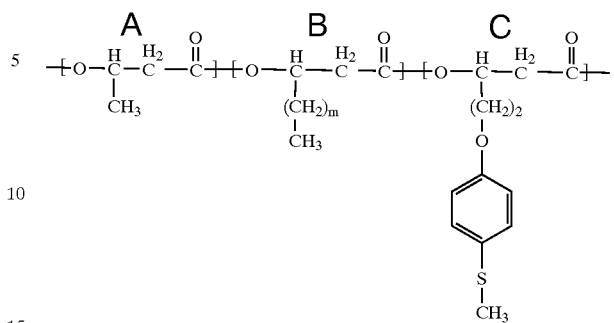

(34)

The molecular weight of the polymer was measured by GPC in the same manner as in Example 1.

Table 19 shows the weight of the obtained microorganism mass, the weight of the polymer, the weight ratio of the polymer to the microorganism mass, and the molecular weight and molecular weight distribution of the polymer.

TABLE 19

| PEG200: 1% | CDW (mg/L) | PDW (mg/L) | P/C (%) | Mn | Mw/Mn |
|---|---|---|---|---|---|
| None | 990 | 150 | 15.2 | 16000 | 2.3 |
| Contained | 1000 | 130 | 13.0 | 9000 | 2.1 |

Example 20
Conversion of Molecular Weight-Controlled Poly 3-hydroxy-5-(phenylsulfanyl)valeric Acid to Poly 3-hydroxy-5-(phenylsulfonyl)valeric Acid:

The homopolymer of 3-hydroxy-5-(phenylsulfanyl)valeric acid (Chemical Formula (20) below) obtained in Example 6 was converted to poly 3-hydroxy-5-(phenylsulfonyl)valeric acid by oxidation treatment.

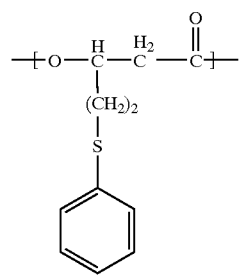

(20)

A 400-mg portion of the polyhydroxyalkanoate was dissolved 10 mL of chloroform in a 100-mL eggplant-shape flask. The flask was placed on an ice bath. Thereto was added slowly a solution of 1386 mg of metachloroperbenzoic acid in 20 mL chloroform, and the mixture was stirred gently. After stirring on the ice bath for 75 minutes, were added thereto 100 mL of water and 3020 mg of sodium hydrogensulfite thereto. The mixture was extracted with chloroform to recover the polymer. The polymer was washed two 100-mL portions of ethanol, and vacuum-dried to obtain intended polymer.

The obtained polymers were subjected to polymer structure determination respectively by ¹H-NMR (FT-NMR: Bruker DPX400; resonance frequency: 400 MHz; measured nuclear species: ¹H; solvent used: CDCl₃; reference:

capillary-sealed TMS/CDCl$_3$; measurement temperature: room temperature). Thereby the polymers were found respectively to be a homopolymer of 3-hydroxy-5-(phenylsulfonyl)valeric acid shown by Chemical Formula (35) below:

(35)

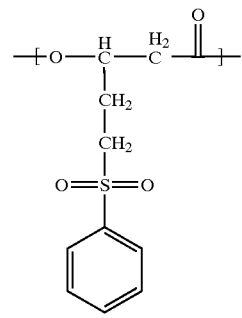

The molecular weight of the polymer was measured by GPC in the same manner as in Example 1.

Table 20 shows the weight of the obtained polymer, and the molecular weight and molecular weight distribution of the polymer.

TABLE 20

| MW controlling agent | Weight (mg) | Mn | Mw/Mn |
|---|---|---|---|
| None | 378 | 135000 | 2.0 |
| 1,2-BD | 366 | 37000 | 1.9 |
| 1,3-BD | 389 | 35000 | 2.1 |
| 1,6-HD | 384 | 26000 | 1.9 |
| 1,2,3-BT | 375 | 42000 | 2.1 |
| EG | 369 | 48000 | 2.0 |
| MEG | 382 | 49000 | 2.1 |

CDW: Dry weight of the microorganism mass
PDW: dry weight of the polymer
P/C: PDW/CDW, Mn: number-average molecular weight
Mw/Mn: molecular weight distribution
1,2-BD: 1,2-butanediol; 1,4-BD: 1,4-butanediol; 1,6-HD: 1,6-hexanediol; 1,2,3-BT: 1,2,3-butanetriol; EG: ethylene glycol; MEG: ethylene glycol monomethyl ether Example 21

Conversion of Molecular Weight-Controlled PHA Containing Units of 3-Hydroxy-5-phenylvaleric Acid and 3-Hydroxy-5-(4-vinylphenyl)valeric Acid by Oxidation Treatment to PHA Containing Units of 3-Hydroxy-5-phenylvaleric Acid and 3-Hydroxy-5-(4-carboxyphenyl) valeric Acid:

The PHA (Chemical Formula 36) obtained in Example 18 containing units of 3-hydroxy-5-phenylvaleric acid and 3-hydroxy-5-(4-vinylphenyl)valeric acid were converted by oxidation treatment to PHA containing units of 3-hydroxy-5-phenylvaleric acid and 3-hydroxy-5-(4-carboxyphenyl) valeric acid.

(36)

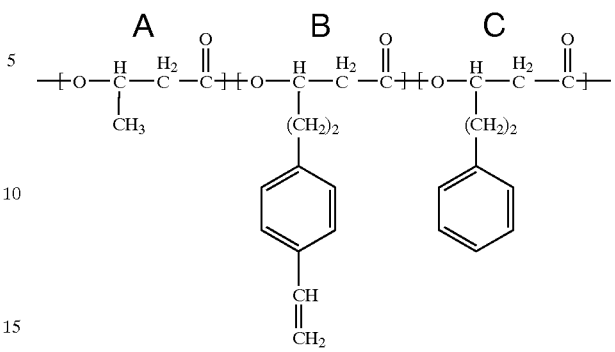

The oxidative cleavage reaction was conducted as follows. In 100-mL flask, were placed 0.3 g of a polyester containing 3-hydroxy-ω-(4-vinylphenyl)alkanoic acid unit, 0.1923 g of 18-crown-6-ether, and 10.0 mL of dichloromethane, and the mixture was stirred. The flask was placed on an ice bath to keep the reaction system at 0° C. After 30 minutes, 0.1517 g of potassium permanganate was added thereto. The reactor flask was wrapped with an aluminum foil and the reaction mixture was stirred for 21 hours. After completion of the reaction, an aqueous solution of sodium hydrogensulfite was added to the reaction mixture, and the reaction mixture was poured in to methanol to reprecipitate and recover the polymer. The obtained polymer was purified by dialysis by use of chloroform.

The structure of the obtained polymer was analyzed by Fourier transform infrared spectroscopy (FT-IR) (Nicolet AV ATAR360 FT-IR). As the result, a new absorption peak of carboxylic acid was observed at 1693 cm$^{-1}$. This shows the presence of 3-hydroxy-ω-(4-carboxyphenyl)alkanoic acid unit in the obtained PHA.

The obtained polymer was allowed to react with trisilyldiazomethane, and the reaction product was analyzed by $^1$H-NMR (FT-NMR: Bruker DPX400; $^1$H resonance frequency: 400 MHz; measured nuclear species: $^1$H; solvent used: CDCl$_3$; reference: capillary-sealed TMS/CDCl$_3$; measurement temperature: room temperature). Thereby the polymer was found to be a hydrorxyalkanoate copolymer containing the unit shown by Chemical Formula (37) below.

(37)

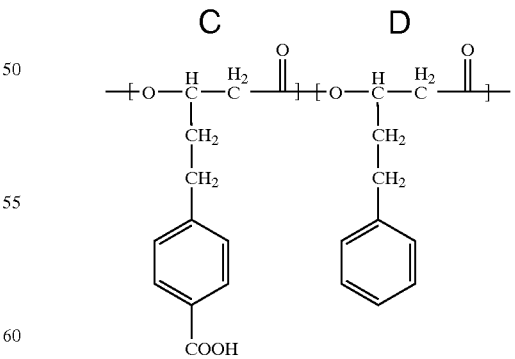

The reaction product of the obtained polymer with trimethylsilyldiazomethane was evaluated for the average molecular weight by gel permeation chromatography (GPC: Tosoh HLC-8220, column: Tosoh TSK-gel Super HM-H, solvent: chloroform, polystyrene basis).

Table 21 shows the weight of the obtained polymer, and the molecular weight and molecular weight distribution of the polymer.

TABLE 21

| PEG200: 1% | Weight (mg) | Mn | Mw/Mn |
|---|---|---|---|
| None | 285 | 32000 | 1.9 |
| Contained | 279 | 10500 | 1.7 |

CDW: Dry weight of the microorganism mass
PDW: dry weight of the polymer
P/C: PDW/CDW, Mn: number-average molecular weight
Mw/Mn: molecular weight distribution Example 22

Molecular weight Control of PHA Containing 3-Hydroxy-5-[(phenylmethyl)oxy]valeric Acid Unit by PEG:

The molecular weight-controlling effect of PEG was evaluated by producing a polymer in the same manner as in Example 8 except that 5-[(phenylmethyl)oxy]valeric acid was used as the polymer-synthesizing substrate.

According to $^1$H-NMR analysis, the obtained polymers were found to be a homopolymer of 3-hydroxy-5-[(phenylmethyl)oxy]valeric acid shown by Chemical Formula (38) below.

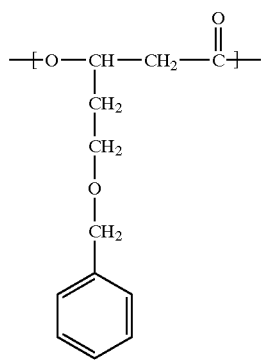

(38)

The molecular weight of the polymer was measured by GPC in the same manner as in Example 1.

Table 22 shows the weight of the obtained microorganism mass, the weight of the polymer, the weight ratio of the polymer to the microorganism mass, and the molecular weight and molecular weight distribution of the polymer.

TABLE 22

| PEG200: 1% | CDW (mg/L) | PDW (mg/L) | P/C (%) | Mn | Mw/Mn |
|---|---|---|---|---|---|
| None | 1350 | 165 | 12.2 | 128000 | 2.4 |
| Contained | 1140 | 125 | 11.0 | 52000 | 2.0 |

What is claimed is:

1. A method for controlling the molecular weight of a polyhydroxyalkanoate containing at least one of a 3-hydroxy-ω-substituted alkanoic acid unit represented by Chemical Formula (1):

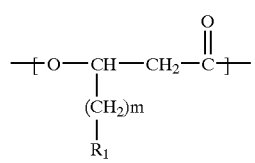

(1)

m = 1–8

(in the above formula, m is an integer selected from the numerical range shown with the Chemical Formula;

$R_1$ is a residue having a ring structure of any one selected from the group consisting of a phenyl structure and a thienyl structure; and in the presence of plural units, m and $R_1$ are selected independently for the respective units), and a 3-hydroxy-ω-cyclohexylalkanoic acid unit represented by Chemical Formula (2):

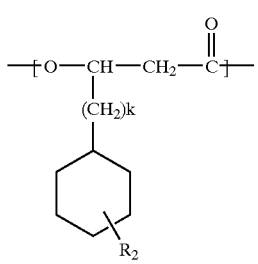

(2)

k = 0–8

(in the above formula, $R_2$ denotes a substituent on the cyclohexyl group selected from the group consisting of H atom, CN, $NO_2$, halogen atom, $CH_3$, $C_2H_5$, $C_3H_7$, $CF_3$, $C_2F_5$ and $C_3F_7$; k is an integer selected from the numerical range shown with the Chemical Formula; and in the presence of plural units, k and $R_2$ are selected independently for the respective units), wherein a microorganism is cultivated, in the presence of a hydroxyl group-containing compound, which is capable of producing the polyhydroxyalkanoate containing at least one of the units represented by Chemical Formula (1) or (2) from an ω-substituted alkanoic acid represented by Chemical Formula (3):

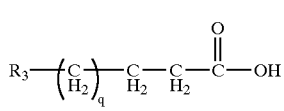

(3)

q = 1–8

(in the above formula, q is an integer selected from the numerical range shown with the Chemical Formula;

$R_3$ is a residue having a ring structure of any one selected from the group consisting of a phenyl structure and a thienyl structure; and in the presence of plural units, q and $R_3$ are selected independently for the respective units), or ω-cyclohexylalkanoic acid represented by Chemical Formula (4):

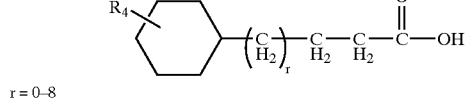

(4)

r = 0–8

(in the above formula, $R_4$ denotes a substituent on the cyclohexyl group selected from the group consisting of H atom, CN, $NO_2$, halogen atom, $CH_3$, $C_2H_5$, $C_3H_7$, $CF_3$, $C_2F_5$ and $C_3F_7$; and r is an integer selected from the numerical range shown with the Chemical Formula; and in the presence of plural units, $R_4$ and r are selected independently for the respective units).

2. The method for controlling the molecular weight of a polyhydroxyalkanoate according to claim 1, wherein $R_1$ and $R_3$ in Chemical Formula (1) and (3) are residues respectively selected from the group consisting of residues represented by Chemical Formulas (5) to (15):

a substituted or unsubstituted phenyl group represented by General Formula (5):

(5)

(in the above formula, $R_5$ denotes a substituent on the aromatic ring selected from the group consisting of H atom, halogen atom, CN, $NO_2$, $CH_3$, $C_2H_5$, $C_3H_7$, vinyl, $COOR_{51}$ (for $R_1$ only; $R_{51}$ is a substituent selected from the group consisting of H atom, Na atom and K atom), $CF_3$, $C_2F_5$ and $C_3F_7$; and in the presence of plural units, the above definition is applied independently of the respective units);

a substituted or unsubstituted phenoxy group represented by General Formula (6):

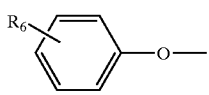

(6)

(in the above formula, $R_6$ denotes a substituent on the aromatic ring selected from the group consisting of H atom, halogen atom, CN, $NO_2$, $CH_3$, $C_2H_5$, $C_3H_7$, $SCH_3$, $CF_3$, $C_2F_5$ and $C_3F_7$; and in the presence of plural units, the above definition is applied independently of the respective units);

a substituted or unsubstituted benzoyl group represented by General Formula (7):

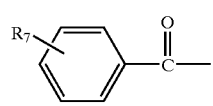

(7)

(in the above formula, $R_7$ denotes a substituent on the aromatic ring selected from the group consisting of H atom, halogen atom, CN, $NO_2$, $CH_3$, $C_2H_5$, $C_3H_7$, $CF_3$, $C_2F_5$ and $C_3F_7$; and in the presence of plural units, the above definition is applied independently of the respective units);

a substituted or unsubstituted phenylsulfanyl group represented by General Formula (8):

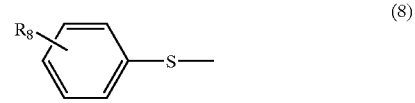

(8)

(in the above formula, $R_8$ denotes a substituent on the aromatic ring selected from the group consisting of H atom, halogen atom, CN, $NO_2$, $COOR_{81}$, $SO_2R_{82}$ ($R_{81}$ is a substituent selected from the group consisting of H, Na, K, $CH_3$ and $C_2H_5$; $R_{82}$ is a substituent selected from the group consisting of OH, ONa, OK, halogen atom, $OCH_3$ and $OC_2H_5$), $CH_3$, $C_2H_5$, $C_3H_7$, $(CH_3)_2$—CH and $(CH_3)_3$—C; and in the presence of plural units, the above definition is applied independently of the respective units);

a substituted or unsubstituted (phenylmethyl)sulfanyl group represented by General Formula (9):

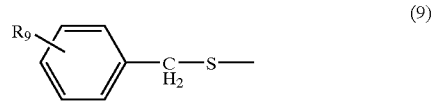

(9)

(in the above formula, $R_9$ denotes a substituent on the aromatic ring selected from the group consisting of H atom, halogen atom, CN, $NO_2$, $COOR_{91}$, $SO_2R_{92}$ ($R_{91}$ is a substituent selected from the group consisting of H, Na, K, $CH_3$ and $C_2H_5$; $R_{92}$ is a substituent selected from the group consisting of OH, ONa, OK, halogen atom, $OCH_3$ and $OC_2H_5$), $CH_3$, $C_2H_5$, $C_3H_7$, $(CH_3)_2$—CH and $(CH_3)_3$—C; and in the presence of plural units, the above definition is applied independently of the respective units);

a 2-thienyl group represented by Chemical Formula (10):

(10)

a 2-thienylsulfanyl group represented by Chemical Formula (11):

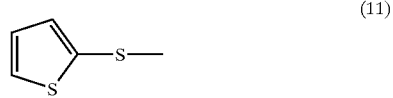

(11)

a 2-thienylcarbonyl group represented by Chemical Formula (12):

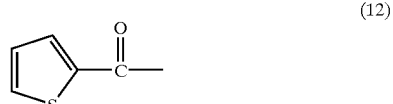

(12)

a substituted or unsubstituted phenylsulfinyl group represented by General Formula (13) (for $R_1$ only):

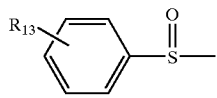

(13)

(in the above formula, $R_{13}$ denotes a substituent on the aromatic ring selected from the group consisting of H atom, halogen atom, CN, $NO_2$, $COOR_{131}$, $SO_2R_{132}$ ($R_{131}$ is a substituent selected from the group consisting of H, Na, K, $CH_3$ and $C_2H_5$; $R_{132}$ is a substituent selected from the group consisting of OH, ONa, OK, halogen atom, $OCH_3$ and $OC_2H_5$), $CH_3$, $C_2H_5$, $C_3H_7$, $(CH_3)_2$—CH and $(CH_3)_3$—C; and in the presence of plural units, the above definition is applied independently of the respective units);

a substituted or unsubstituted phenylsulfonyl group represented by General Formula (14) (for $R_1$ only):

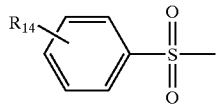

(14)

(in the above formula, $R_{14}$ denotes a substituent on the aromatic ring selected from the group consisting of H atom, halogen atom, CN, $NO_2$, $COOR_{141}$, $SO_2R_{142}$ ($R_{141}$ representing H, Na, K, $CH_3$ and $C_2H_5$; $R_{142}$ is a substituent selected from the group consisting of OH, ONa, OK, halogen atom, $OCH_3$ and $OC_2H_5$), $CH_3$, $C_2H_5$, $C_3H_7$, $(CH_3)_2$—CH and $(CH_3)_3$—C; and in the presence of plural units, the above definition is applied independently of the respective units); and a (phenylmethyl)oxy group represented by Chemical Formula (15):

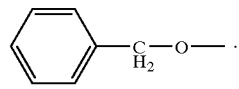

(15)

3. The method for controlling the molecular weight of a polyhydroxyalkanoate according to claim 1, wherein the hydroxyl group-containing compound is at least the one selected from the group consisting of alcohols, diols, triols, alkylene glycols, polyethylene glycols, polyethylene oxides, alkylene glycol monoesters, polyethylene glycol monoesters, and polyethylene oxide monoesters.

4. The method for controlling the molecular weight of a polyhydroxyalkanoate according to claim 3, wherein the alcohols, diols, and triols have a linear or branched structure of 3–14 carbons.

5. The method for controlling the molecular weight of a polyhydroxyalkanoate according to claim 3, wherein the alkylene glycols and alkylene glycol monoesters have a linear or branched structure of 2–10 carbons, respectively.

6. The method for controlling the molecular weight of a polyhydroxyalkanoate according to claim 3, wherein the polyethylene glycols, polyethylene oxides, polyethylene glycol monoesters, and polyethylene oxide monoesters have a number-average molecular weight ranging from 100 to 20000, respectively.

7. The method for controlling the molecular weight of a polyhydroxyalkanoate according to claim 1, wherein the hydroxyl group-containing compound is used in the cultivation of the microorganism at a concentration from 0.01 to 10%(w/v).

8. The method for controlling the molecular weight of a polyhydroxyalkanoate according to claim 1, wherein the microorganism belongs to Pseudomonas genus.

9. The method for controlling the molecular weight of a polyhydroxyalkanoate according to claim 8, wherein the one or more of *Pseudomonas cichorii* YN2 (FERM BP-7375), *Pseudomonas cichorii* $H_{45}$ (FREM BP-7374), *Pseudomonas jessenii* P161 (FERM BP-7376), and *Pseudomonas putida* P91 (FREM BP-7373).

10. A polyhydroxyalkanoate, which contains at least one of a 3-hydroxy-ω-substituted-alkanoic acid unit represented by Chemical Formula (16):

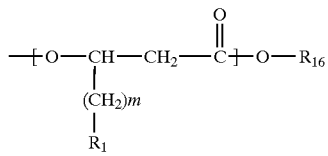

m = 1–8

(in the above formula, m is an integer selected from the numerical range shown with the Chemical Formula;

$R_1$ is a residue having a ring structure of any one selected from the group consisting of a phenyl structure and a thienyl structure; in the presence of plural units, m and $R_1$ are selected independently for the respective units; and $R_{16}$ is a group derived from a chemical species selected from the group consisting of alcohols, diols, triols, alkylene glycols, polyethylene glycols, polyethylene oxides, alkylene glycol monoesters, polyethylene glycol monoesters, and polyethylene oxide monoesters), and a 3-hydroxy-ω-cyclohexylalkanoic acid unit represented by General formula (17):

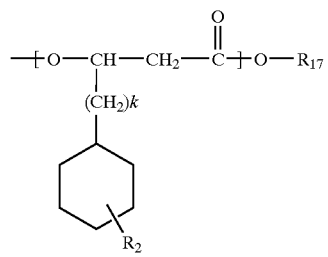

k = 0–8

(in the above formula, $R_2$ denotes a substituent on the cyclohexyl group selected from the group consisting of H atom, CN, $NO_2$, halogen atom, $CH_3$, $C_2H_5$, $C_3H_7$, $CF_3$, $C_2F_5$ and $C_3F_7$; k is an integer selected from the numerical range shown with the Chemical Formula;

in the presence of plural units, k and $R_2$ are selected independently for the respective units; and $R_{17}$ is a group derived from a chemical species selected from the group consisting of alcohols, diols, triols, alkylene glycols, polyethylene glycols, polyethylene oxides, alkylene glycol monoesters, polyethylene glycol monoesters, and polyethylene oxide monoesters).

11. The polyhydroxyalkanoate according to claim 10, wherein $R_1$ in Chemical Formula (16) is a residue selected from the group consisting of residues represented by Chemical Formulas (5) to (15):

a substituted or unsubstituted phenyl group represented by General Formula (5):

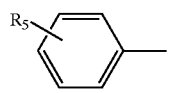
(5)

(in the above formula, $R_5$ denotes a substituent on the aromatic ring selected from the group consisting of H atom, halogen atom, CN, $NO_2$, $CH_3$, $C_2H_5$, $C_3H_7$, vinyl, $COOR_{51}$ (for $R_1$ only; $R_{51}$ is a substituent selected from the group consisting of H atom, Na atom and K atom), $CF_3$, $C_2F_5$ and $C_3F_7$; and in the presence of plural units, the above definition is applied independently of the respective units);

a substituted or unsubstituted phenoxy group represented by General Formula (6):

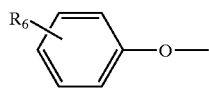
(6)

(in the above formula, $R_6$ denotes a substituent on the aromatic ring selected from the group consisting of H atom, halogen atom, CN, $NO_2$, $CH_3$, $C_2H_5$, $C_3H_7$, $SCH_3$, $CF_3$, $C_2F_5$ and $C_3F_7$; and in the presence of plural units, the above definition is applied independently of the respective units);

a substituted or unsubstituted benzoyl group represented by General Formula (7):

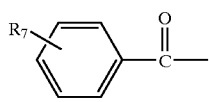
(7)

(in the above formula, $R_7$ denotes a substituent on the aromatic ring selected from the group consisting of H atom, halogen atom, CN, $NO_2$, $CH_3$, $C_2H_5$, $C_3H_7$, $CF_3$, $C_2F_5$ and $C_3F_7$; and in the presence of plural units, the above definition is applied independently of the respective units);

a substituted or unsubstituted phenylsulfanyl group represented by General Formula (8):

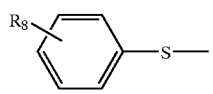
(8)

(in the above formula, $R_8$ denotes a substituent on the aromatic ring selected from the group consisting of H atom, halogen atom, CN, $NO_2$, $COOR_{81}$, $SO_2R_{82}$ ($R_{81}$ is a substituent selected from the group consisting of H, Na, K, $CH_3$ and $C_2H_5$; $R_{82}$ is a substituent selected from the group consisting of OH, ONa, OK, halogen atom, $OCH_3$ and $OC_2H_5$), $CH_3$, $C_2H_5$, $C_3H_7$, $(CH_3)_2$—CH and $(CH_3)_3$—C; and in the presence of plural units, the above definition is applied independently of the respective units);

a substituted or unsubstituted (phenylmethyl)sulfanyl group represented by General Formula (9):

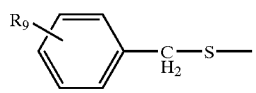
(9)

(in the above formula, $R_9$ denotes a substituent on the aromatic ring selected from the group consisting of H atom, halogen atom, CN, $NO_2$, $COOR_{91}$, $SO_2R_{92}$ ($R_{91}$ is a substituent selected from the group consisting of H, Na, K, $CH_3$ and $C_2H_5$; $R_{92}$ is a substituent selected from the group consisting of OH, ONa, OK, halogen atom, $OCH_3$ and $OC_2H_5$), $CH_3$, $C_2H_5$, $C_3H_7$, $(CH_3)_2$—CH and $(CH_3)_3$—C; and in the presence of plural units, the above definition is applied independently of the respective units);

a 2-thienyl group represented by Chemical Formula (10):

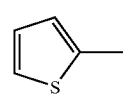
(10)

a 2-thienylsulfanyl group represented by Chemical Formula (11):

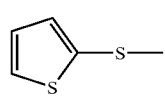
(11)

a 2-thienylcarbonyl group represented by Chemical Formula (12):

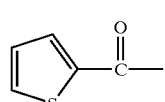
(12)

a substituted or unsubstituted phenylsulfinyl group represented by General Formula (13) (for $R_1$ only):

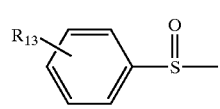
(13)

(in the above formula, $R_{13}$ denotes a substituent on the aromatic ring selected from the group consisting of H atom, halogen atom, CN, $NO_2$, $COOR_{131}$, $SO_2R_{132}$ ($R_{131}$ is a substituent selected from the group consisting of H, Na, K, $CH_3$ and $C_2H_5$; $R_{132}$ is a substituent selected from the group consisting of OH, ONa, OK, halogen atom, $OCH_3$ and $OC_2H_5$), $CH_3$, $C_2H_5$, $C_3H_7$, $(CH_3)2$—CH and $(CH_3)_3$—C; and in the presence of plural units, the above definition is applied independently of the respective units);

a substituted or unsubstituted phenylsulfonyl group represented by General Formula (14) (for $R_1$ only):

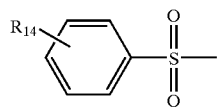
(14)

(in the above formula, $R_{14}$ denotes a substituent on the aromatic ring selected from the group consisting of H atom, halogen atom, CN, $NO_2$, $COOR_{141}$, $SO_2R_{142}$ ($R_{141}$ representing H, Na, K, $CH_3$ and $C_2H_5$; $R_{142}$ is a substituent selected from the group consisting of OH, ONa, OK, halogen atom, $OCH_3$ and $OC_2H_5$), $CH_3$, $C_2H_5$, $C_3H_7$, $(CH_3)_2$—CH and $(CH_3)_3$—C; and in the presence of plural units, the above definition is applied independently of the respective units); and a (phenylmethyl)oxy group represented by Chemical Formula (15):

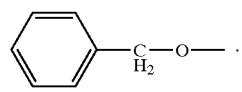
(15)

12. The method according to claim 7 wherein the concentration is from 0.02 to 5% (w/v).

* * * * *

UNITED STATES PATENT AND TRADEMARK OFFICE
CERTIFICATE OF CORRECTION

PATENT NO. : 6,649,380 B1
DATED : November 18, 2003
INVENTOR(S) : Tetsuya Yano et al.

It is certified that error appears in the above-identified patent and that said Letters Patent is hereby corrected as shown below:

Title page, Item [54] and Column 1, lines 3, 4 and 5,
Title, "POLYHYDROXYALKANOTE" should read
-- POLYHYDROXYALKANOATE --; "ON" should read -- OF --; and
"PHEYNYL-," should read -- PHENYL-, --.

Title page,
Item [56], References Cited, OTHER PUBLICATIONS, after
"Joanne M. Curley et al." reference, "*Pseudomaonas oleovorans*," should read
-- *Pseudomonas oleovorans*, --; "Ohyoung Kim et al.," reference, "Incorprated" should
read -- Incorporation --; and "Yasuo Takagi et al.," reference, "Groups" should read
-- Group --.
Item [57], ABSTRACT,
Line 5, "$-[OCH((CH_2)_kC_6H_{1)}R_2)CH_2C$" should read -- $-[OCH((CH_2)_kC_6H_{10}R_2)CH_2C$ --.

Column 1,
Line 30, "diodegradable" should read -- biodegradable --.

Column 2,
Line 22, "$(3H_5(MHP)P)$" should read -- (3H5(MHP)P) --;
Line 23, "$(3H_5(DHP)P)$" should read -- (3H5(DHP)P) --;
Line 24, "$3H_5(MFP)P$" should read -- 3H5(MFP)P -- and "$3H_5$" should read
-- 3H5(DFP)P --;
Line 24, "(DFP)P" should be deleted;
Line 25, "*Psudomonas putida*" should read -- *Pseudomonas putida* --; and
Line 26, "(Pseudomanas Genus);" should read -- (Genus *Pseudomonas*); --.

Column 3,
Line 9, "provide" should read -- provides --.

Column 4,
Line 33, "Here, $R_1$, and" should read -- Here, $R_1$ and --.

Column 6,
Lines 17 and 35, "only)" should read -- only): --.

Column 7,
Line 50, "General formula (17):" should read -- General Formula (17): --.

UNITED STATES PATENT AND TRADEMARK OFFICE
CERTIFICATE OF CORRECTION

PATENT NO. : 6,649,380 B1
DATED : November 18, 2003
INVENTOR(S) : Tetsuya Yano et al.

It is certified that error appears in the above-identified patent and that said Letters Patent is hereby corrected as shown below:

Column 8,
Line 20, "(4)" should read -- (4). --;
Line 41, "3-Hydorxyacyl-CoA" should read -- 3-Hydroxyacyl-CoA --;
Line 50, "FEMS microbiology Reviews," should read -- FEMS Microbiology Reviews, --; and
Line 57, "Micromolecules" should read -- Macromolecules --.

Column 9,
Line 3, "*Peudomonas jessenii*," should read -- *Pseudomonas jessenii*, --;
Line 5, "*cichori* YN2" should read -- *cichorii* YN2 --;
Line 6, "(FREM BP-7374)," should read -- (FERM BP-7374), --; and
Line 7, "(FREM BP-7373)." should read -- (FERM BP-7373). --.

Column 10,
Line 12, "most" should be deleted; and
Line 31, "resent" should read -- present --.

Column 11,
Line 7, "24 hour" should read -- 24 hours --.

Column 14,
Line 29, "Cutivation" should read -- Cultivation --.

Column 16,
Line 65, "hompopolymer" should read -- homopolymer --.

Column 18,
Line 62, "5-phnoxyvaleric" should read -- 5-phenoxyvaleric --.

Column 20,
Line 19, "3-hydroxy-5-phnoxyvaleric" should read -- 3-hydroxy-5-phenoxyvaleric --.

Column 21,
Line 41, "3-hydroxy-5-phnoxyvaleric" should read -- 3-hydroxy-5-phenoxyvaleric --.

Column 26,
Line 54, "eggplant-shape" should read -- eggplant-shaped --; and
Line 62, "two" should read -- with two --.

UNITED STATES PATENT AND TRADEMARK OFFICE
CERTIFICATE OF CORRECTION

PATENT NO. : 6,649,380 B1
DATED : November 18, 2003
INVENTOR(S) : Tetsuya Yano et al.

It is certified that error appears in the above-identified patent and that said Letters Patent is hereby corrected as shown below:

Column 28,
Line 19, "In 100-mL flask," should read -- In a 100-mL flask, --;
Line 29, "in to" should read -- into --; and
Line 44, "hydrorxyalkanoate" should read -- hydroxyalkanoate --.

Column 29,
Line 18, "Molecular weight Control" should read -- Molecular Weight Control --.

Column 34,
Line 8, "wherein the" should read -- wherein the microorganism is --;
Line 10, "$H_{45}$(FREM BP-7374)," should read -- H45 (FERM BP-7374), --;
Line 12, "(FREM BP-7373)." should read -- (FERM BP-7373). --;
Line 34, insert -- (16) --;
Line 37, "General formula (17):" should read -- General Formula (17): --; and
Line 50, insert -- (17) --.

Column 38,
Line 13, "claim 7" should read -- claim 7, --.

Signed and Sealed this

Twenty-seventh Day of July, 2004

JON W. DUDAS
*Acting Director of the United States Patent and Trademark Office*